(12) United States Patent
Arinzeh et al.

(10) Patent No.: US 9,192,655 B2
(45) Date of Patent: Nov. 24, 2015

(54) SYSTEM AND METHOD FOR A HYDROGEL AND HYDROGEL COMPOSITE FOR CARTILAGE REPAIR APPLICATIONS

(75) Inventors: Treena Arinzeh, West Orange, NJ (US); George Collins, Maplewood, NJ (US); Bruno Mantilla, Edison, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 110 days.

(21) Appl. No.: 12/661,242

(22) Filed: Mar. 12, 2010

(65) Prior Publication Data

US 2010/0233234 A1 Sep. 16, 2010

Related U.S. Application Data

(60) Provisional application No. 61/159,747, filed on Mar. 12, 2009.

(51) Int. Cl.
| | | |
|---|---|---|
| *A61K 38/39* | (2006.01) | |
| *A61F 2/00* | (2006.01) | |
| *A01N 63/00* | (2006.01) | |
| *A61K 35/28* | (2015.01) | |
| *A61L 27/26* | (2006.01) | |
| *A61L 27/52* | (2006.01) | |
| *C08L 1/02* | (2006.01) | |
| *D01D 5/00* | (2006.01) | |
| *D01F 2/24* | (2006.01) | |

(52) U.S. Cl.
CPC .............. *A61K 38/39* (2013.01); *A61K 35/28* (2013.01); *A61L 27/26* (2013.01); *A61L 27/52* (2013.01); *C08L 1/02* (2013.01); *D01D 5/0007* (2013.01); *D01F 2/24* (2013.01); *A61L 2430/06* (2013.01)

(58) Field of Classification Search
None
See application file for complete search history.

(56) References Cited

U.S. PATENT DOCUMENTS

| | | |
|---|---|---|
| 4,846,835 A | 7/1989 | Grande |
| 5,030,225 A | 7/1991 | Aebischer et al. |
| 5,250,843 A | 10/1993 | Eichelberger |
| 5,353,498 A | 10/1994 | Fillion et al. |
| 5,486,359 A | 1/1996 | Caplan |
| 5,522,879 A | 6/1996 | Scopelianos |
| 5,626,861 A | 5/1997 | Laurencin et al. |
| 5,666,467 A | 9/1997 | Colak |
| 5,681,873 A | 10/1997 | Norton et al. |
| 5,766,618 A | 6/1998 | Laurencin et al. |
| 5,811,094 A | 9/1998 | Caplan |
| 5,827,735 A | 10/1998 | Young |
| 5,841,193 A | 11/1998 | Eichelberger |
| 5,906,934 A | 5/1999 | Grande et al. |
| 5,955,529 A | 9/1999 | Imai et al. |
| 6,095,148 A | 8/2000 | Shastri et al. |
| 6,165,486 A | 12/2000 | Marra et al. |
| 6,174,333 B1 | 1/2001 | Kadiyala et al. |
| 6,214,369 B1 | 4/2001 | Grande et al. |
| 6,306,424 B1 | 10/2001 | Vyakarnam |
| 6,355,239 B1 | 3/2002 | Bruder |
| 6,387,367 B1 | 5/2002 | David-Sproul |
| 6,464,983 B1 | 10/2002 | Grotendorst |
| 6,472,210 B1 | 10/2002 | Holy et al. |
| 6,482,231 B1 | 11/2002 | Abatangelo |
| 6,489,165 B2 | 12/2002 | Bhatnager et al. |
| 6,511,511 B1 | 1/2003 | Slivka et al. |
| 6,541,024 B1 | 4/2003 | Kadiyala |
| 6,685,956 B2 | 2/2004 | Chu |
| 6,689,166 B2 | 2/2004 | Laurencin |
| 6,689,374 B2 | 2/2004 | Chu |
| 6,730,252 B1 | 5/2004 | Teoh et al. |
| 6,783,712 B2 | 8/2004 | Slivka et al. |
| 6,790,455 B2 | 9/2004 | Chu |
| 6,790,528 B2 | 9/2004 | Wendorff |
| 6,863,900 B2 | 3/2005 | Kadiyala |
| 7,012,106 B2 | 3/2006 | Yuan et al. |
| 7,022,522 B2 | 4/2006 | Guan et al. |
| 7,247,313 B2 | 7/2007 | Roorda et al. |
| 7,271,234 B2 | 9/2007 | Kohn et al. |
| 7,601,525 B2 | 10/2009 | Batich et al. |
| 7,619,901 B2 | 11/2009 | Eichelberger et al. |
| 7,767,221 B2 | 8/2010 | Lu et al. |
| 7,803,574 B2 | 9/2010 | Desai |

(Continued)

FOREIGN PATENT DOCUMENTS

| | | |
|---|---|---|
| WO | WO 2006/068809 | 6/2006 |
| WO | WO 2006095021 A1 | 9/2006 |

(Continued)

OTHER PUBLICATIONS

Friedenstein, A. et al., Bone Marrow Osteogenetic Stem Cells: In Vitro Cultivation and Transplantation in Diffusion Chambers, Cell Tissue Kinet, 1987, 20(3):263-72.

Safronova, E. E. et al., Characteristics of the macromolecular components of the extracellular matrix in human hyaline cartilage at different stages of ontogenesis, Biomedical Science, 1991, 2:162-8.

Haynesworth, S. et al., Cell Surface Antigens on Human Marrow-Derived Mesenchymal Stem Cells are Detected by Monoclonal Antibodies, J. Cell Physiol., 1992, 138:8-16.

Rickard, D. J. et al., Induction of rapid osteoblast differentiation in rat bone marrow stromal cell cultures by dexamethason and BMP-2, Dev. Bio., 1994, 161:218-28.

Jaiswal, N. et al., Osteogenic differentiation of purified culture-expanded human mesenchymal stem cells in vitro, J. Cell Biochem., 1997, 64:295-312.

(Continued)

*Primary Examiner* — Dennis J Parad
(74) *Attorney, Agent, or Firm* — McCarter & English, LLP

(57) ABSTRACT

The embodiments and examples provided herein are put forth so as to provide those of ordinary skill in the art with a complete disclosure and description of how to make and use the present invention, and are not intended to limit the present invention relates to compositions and methods of preparing a hydrogel comprising a water soluble cellulose compound, as well as preparing a three-dimensional matrix of micron sized electrospun fibers, wherein the electrospun fibers are formed from a electrospun composite comprising a water soluble cellulose compound. The matrix provides a scaffold supporting and promoting cartilage regeneration and repair.

15 Claims, 13 Drawing Sheets
(10 of 13 Drawing Sheet(s) Filed in Color)

(56) References Cited

U.S. PATENT DOCUMENTS

| | | |
|---|---|---|
| 2002/0004039 A1 | 1/2002 | Reid et al. |
| 2002/0034796 A1 | 3/2002 | Shastri et al. |
| 2002/0173213 A1 | 11/2002 | Chu et al. |
| 2003/0054035 A1 | 3/2003 | Chu et al. |
| 2003/0069369 A1 | 4/2003 | Belenkaya et al. |
| 2003/0077311 A1 | 4/2003 | Vyakarnam et al. |
| 2003/0211130 A1 | 11/2003 | Sanders et al. |
| 2004/0018226 A1 | 1/2004 | Wnek |
| 2005/0095695 A1 | 5/2005 | Shindler et al. |
| 2005/0196423 A1 | 9/2005 | Batich et al. |
| 2006/0057377 A1 | 3/2006 | Harrison et al. |
| 2006/0094320 A1 | 5/2006 | Chen et al. |
| 2006/0128012 A1 | 6/2006 | Arinzeh |
| 2006/0198865 A1* | 9/2006 | Freyman et al. ............... 424/423 |
| 2006/0204539 A1 | 9/2006 | Atala |
| 2006/0240064 A9 | 10/2006 | Hunter et al. |
| 2007/0179594 A1 | 8/2007 | Llanos et al. |
| 2007/0267725 A1 | 11/2007 | Lee et al. |
| 2008/0009599 A1 | 1/2008 | Esat et al. |
| 2008/0112150 A1 | 5/2008 | Jones |
| 2008/0206343 A1 | 8/2008 | Edinger et al. |
| 2008/0246126 A1 | 10/2008 | Bowles et al. |
| 2009/0028921 A1 | 1/2009 | Arinzeh |
| 2009/0048358 A1 | 2/2009 | Kim |
| 2009/0325296 A1 | 12/2009 | Arinzeh |
| 2010/0078771 A1 | 4/2010 | Barth et al. |
| 2010/0078776 A1 | 4/2010 | Barth et al. |
| 2010/0173158 A1 | 7/2010 | Furuzono et al. |
| 2010/0233234 A1 | 9/2010 | Arinzeh |
| 2010/0233807 A1 | 9/2010 | Arinzeh |
| 2010/0324697 A1 | 12/2010 | Arinzeh |
| 2011/0274742 A1 | 11/2011 | Arinzeh |
| 2011/0300626 A1 | 12/2011 | Arinzeh |
| 2013/0052254 A1 | 2/2013 | Arinzeh |

FOREIGN PATENT DOCUMENTS

| | | |
|---|---|---|
| WO | WO 2008/055038 A2 | 5/2008 |
| WO | WO 2008055038 A2 * | 5/2008 |
| WO | WO 2008/157594 | 12/2008 |
| WO | WO 2013/023064 | 2/2013 |

OTHER PUBLICATIONS

Kadiyala, S. et al., Culture-expanded, bone marrow-derived mesenchymal stem cells can regenerate a critical-sized segmental bone defect, Tissue Engineering, 1997, 3(2):173-185.
Mackay, A. M. et al., Chrondrogenic differentiation of cultured human mesenchymal stem cells from marrow, Tissue Engineering, 1998, 4(4):415-428.
Brudner, S. P. et al., Bone Regeneration by Implantation of Purified, Culture-Expanded Human Mesenchymal Stem Cells, J. Orthop. Res., 1998, 16:155-162.
Praemer, A., Musculoskeletal conditions in the United States, American Academy of Orthopaedic Surgeons, 1999, p. 34-39.
Pittenger, M. F. et al., Multilineage potential of adult human mesenchymal stem cells, Science, 1999, 284:143-7.
Browne, J. E. et al., Surgical alternatives for treatment of articular cartilage lesions, J. Am. Acad. Orthop. Surg., 2000, 8(3):180-9.
Xie, L. et al., A niche maintaining germ line stem cells in the *Drosophila* ovary, Science, 2000, 290(5490):328.
Fuchs, E. et al., Stem cells: a new lease on life, Cell, 2000, 100:143-55.
Watt, F. M. et al., Out of eden: stem cells and their niches, Science, 2000, 287(5457):1427.
DeLise, A. M. et al., Cellular interactions and signaling in cartilage development, Osteoarthritis and Cartilage, 2000, 8:309-34.
Christensen, N. D. et al., Papillomavirus microbicidal activities of high-molecular-weight cellulose sulfate, dextran sulfate, and polystyrene sulfonate, Antimicrobial Agents and Chemotherapy, 2001, 45(12):3427-32.
Ishihara, M. et al., Heparin-carrying polystyrene (HCPS)-bound collagen substratum to immobilize heparin-binding growth factors and to enhance cellular growth, J. Biomed. Mat. Res., 2001, 56(4):536-44.
Rogovina, S. Z. et al., Solid state production of cellulose-chitosan blends and their modification and the diglycidyl ether of oligo(ethylene oxide), Polymer Degradation and Stability, 2001, 73(3):557-60.
Barry, F. et al., Chondrogenic differentiation of mesenchymal stem cells from bone marrow: differentiation-dependent gene expression of matrix components, Experimental Cell Research, 2001, 268:189-200.
Dozin, B. et al., Response of young, aged and osteoarthritic human articular chondrocytes to inflammatory cytokines: molecular and cellular aspects, Matrix Biology, 2002, 21(5):449-59.
Anderson, R. A. et al., Preclinical evaluation of sodium cellulose sulfate (Ushercell) as a contraceptive antimicrobial agent, Journal of Andrology, 2002, 23(3):426-38.
Arinzeh, T. et al.,In vivo evaluation of a bioactive scaffold for bone tissue engineering, J. Biomed. Mat. Res., 2002, 62:1-13.
Muller, P. Y. et al., Processing of gene expression data generated by quantitative real-time RT-PCR, Biotechniques, 2002, 32(6):1372-4.
Nettles et al., Potential Use of Chitosan as a Cell Scaffold Material for Carilage Tissue Engineering, Tissue Engineering, Vo.. 8, No. 6, pp. 1009-1016, 2002.
Endres et al., Osteogenic Induction of Human Bone Marrow-Derived Mesenchymal Progenitor Cells in Novel Synthetic Polymer-Hydrogel Matrices, Tissue Engineering, vol. 9, No. 4, pp. 689-702, 2003.
Arinzeh, T. et al, Allogeneic mesenchymal stem cells regenerate bone in a critical-sized canine segmental defect, Journal of Bone and Joint Surgery American, 2003, 85-A(1):1927-35.
Sittinger et all., Current Strategies for Cell Delivery in Cartilage and Bone Regeneration, Current Opinion in Biotechnology, vol. 115, Issue 5, pp. 411-418, 2004.
Shields, K. J. et al., Mechanical properties and cellular proliferation of electrospun collagen Type II, Tissue Engineering, 2004, 10(9-10):1510-7.
You, J. O. et al., Calcium-alginate nanoparticles formed by reverse microemulsion as gene carriers, macromolecular Symposia, 2004, 219(147):153.
Browne, J. E. et al., Clinical outcome of autologous chondrocyte implantation at 5 years in US subjects, Clinical Orthopaedics and Related Research, 2005, 436:237-45.
Kang, S. W. et al., Ply(lactic-co-glycolic acid) microspheres as an injectible scaffold for cartilage tissue engineering, Tissue Engineering, 2005, 11(3-4):438-47.
Clar, C. et al., Clinical and cost-effectiveness of autologous chondocyte implantation for cartilage defects in knee joints: systematic review and economic evaluation, Health Technology Assessment, 2005, 9(47):4 pages.
Maire, M. et al., Retention of transforming growth factor using functionalized dextran-based hydrogels, Biomaterials, 2005, 26(14):1771-80.
Schaffellner, S. et al., Porcine islet cells microencapsulated in sodium cellulose sulfate, Transplantation Proceedings, 2005, 37(1):248-52.
Li, W. J. et al., Multilineage differentiation of human mesenchymal stem cells in a three-dimensional nanofibrous scaffold, Biomaterials, 2005, 26(5):5158-66.
Kuo, C. K. et al., Cartilage tissue engineering: its potential and uses, Current Opinion in Rheumatology, 2006, 18(1):64-73.
Pelttari, K. et al., Premature induction of hypertrophy during in vitro chondrogenesis of human mesenchymal stem cells correlates with calcification and vascular invasion after ectopic transplantation in SCID mice, Arthritis and Rheumatism, 2006, 54:3254-3266.
Shanmugasundaram, S. et al., The Effect of Varying the Architecture of Scaffolds on Mesenchymal Stem Cell Osteogenesis and Chondrogenesis, Transactions of the 2006 Annual Meeting of the Society for Biomaterials, 2006.
Gama, C. L., Sulfation patterns of glycosaminoglycans encode molecular recognition and activity, Nature Chemical Biology, 2006, 2(9):467-473.
Stiegler, P. B. et al., Cryopreservation of insulin-producing cells microencapsulated in sodium cellulose sulfate, Transplantation Proceedings, 2006, 38(9):3026-3030.

(56) References Cited

OTHER PUBLICATIONS

Li, W. J. et al., Fabrication and characterization of six electrospun poly(alpha-hydroxyester)-based fibrous scaffolds for tissue engineering applications, Acta Biomaterialia, 2006, 2(4):377-385.
Karlsson, C. et al., Differentiation of human mesenchymal stem cells and articular chondrocytes: analysis of chondrogenic potential and expression pattern of differentiation-related transcription factors, Journal of Orthopaedic Research, 2007, 25:152-163.
Chamberlain, G. et al., Concise review: mesenchymal stem cells: their phenotype, differentiation capacity, immunological features, and potential for homing, Stem Cells, 2007, 25(11):2739-2749.
Xin, X. et al., Continuing differentiation of human mesenchymal stem cells and induced chondrogenic and osteogenic lineages in electrospun PLGA nanofiber scaffold, Biomaterials, 2007, 28(2):316-325.
Greco, S. et al., An interdisciplinary approach and characterization of neuronal cells transdifferentiated from human mesenchymal stem cells, Stem cells and development, 2007, 16(5):811-826.
Temple, M. M. et al., Age- and site-associate biomechanical weakening of human articular cartilage of the femoral condyle, Osteoarthritis and Cartilage, 2007, 15:1042-1052.
Lack, S. et al., High-resolution nuclear magnetic resonance spectroscopy studies of polysaccharides crosslinked by sodium trimetaphosphate: a proposal for the reaction mechanism, Carbohydrate Research, 2007, 342(7):943-953.
Collins, M. N. et al., Comparison of the effectiveness of four different crosslinking agents with hyaluronic acid hydrogel films for tissue-culture applications, Journal of Applied Polymer Science 2007, 104(5):3183-3191.
Greco, S. J. et al., Functional similarities among genes regulated by oct-4 in human mesenchymal and embryonic stem cells, Stem Cells, 2007, 25(12:3143-3154.
Mueller, M. B. et al., Functional characterization of hypertrophy in chondrogenesis of human mesenchymal stem cells, Arthritis and Rheumatism, 2008, 58(5):1377-88.
Forsten-Williams, K., et al., Control of growth factor networks by heparin sulfate proteoglycans, Annals of Biomedical Engineering, 2008, 36(12):2134-48.
Magnussen, R. A. et al., Treatment of focal articular cartilage defects in the knee: a systematic review, Clinical Orthopaedics and Related Research, 2008, 466(4):952-62.
Chondrogen clinical trial information for the treatment of knee injuries, Osiris Therapeutics, Inc., 2008, Ref. Type: Internet Communication.
Liu, Z. et al., Polysaccharides-based nanoparticles as drug delivery systems, Advanced Drug Delivery Reviews, 2008, 60(15):1650-62.
Bian, L. et al., Influence of chondoitin sulfate on the biochemical, mechanical and frictional properties of cartilage explants in long-term culture, Journal of Biomechanics, In press 2008.
Chen, Y. et al., Development of a chitosan-based nanoparticle formulation for delivery of a hydrophilic hexapeptide, dalargin, Biopolymers, 2008, 90(5):663-670.
Shanmugasundaram, S. et al., Regulation of human mesenchymal stem cell chondrogenesis by scaffold geometry and mechanical properties, Society for Biomaterials Annual Meeting, 2009.
Shanmugasundaram, et al., Microscale Versus Nanoscale Scaffold Architecture for Mesenchymal Stem Cell Chondrogenesis, Tissue Engineering: Part A, vol. 60, No. 00, 2010, pp. 1-10.
Rosenzweig, et al., Rodent Models for Treatment of Spinal Cord Injury: Research Trends and Progress Toward Useful Repair, Current Opinion in Neurology, 17(2); 121-31, 2004.
Shanmugasundaram, et al., Applications of Electrospinning: Tissue Engineering Scaffolds and Drug Delivery System, Bioengineering, Proceedings of the Northeast Conference, vol. 30, pp. 140-141, 2004.
Shin et al., In Vivo Bone Tissue Engineering Using Mesenchymal Stem Cells on a Novel Electrospun Nanofibrous Scaffold, Tissue Engineering, 10, pp. 33-41, 2004.
Wei et al., Structural and Properties of Nano-Hydroxyapatite/Polymer Composite Scaffolds for Bone Tissue Engineering, Biomaterials, 25, pp. 4749-4757, 2004.
Arinzeh et al., A Comparative Study of Biphasic Calcium Phosphate Ceramics for Human Mesenchymal Stem-Cell-induced Bone Formation, Biomaterials, 26(17): 3631-8, 2005.
Aroen, A. et al, "Articular Cartilage Defects in a Rabbit Model, Retention Rate of Periosteal Flap Cover", Acta Orthop. 76(2):220-4, 2005.
Cummings, et al., Human Neural Stem Cells Differentiate and Promote Locomoter Recovery in Spinal Cord-Injured Mice, Proceedings of the National Academy of Sciences, 102(39):14069-74, 2005.
Ducharme, et al., Ferroelectric Polymeric Langmuir-Blodgett Films for Non-Volatile Memory Applications, Nebraska Research Initiative, the National Science Foundation and the Office of Naval Research, Department of Physics and Astronomy and the Center for Materials Research and Analysis at the University of Nebraska, Lincoln, NE, pp. 1-41, 2005.
Fujihara, et al., Guided Bone Regeneration Membrane Made of Polycaprolactone/Calcium Carbonate Composite Nano-fibers, Biomaterials, 26, pp. 4139-4147, 2005.
Holmes, N. "CD45: All is Not Yet Crystal Clear", Immunology 117:145-155, 2005.
Klein, et al., Influence of Composition on Relaxor Ferroelectric and Electromechanical Properties of Poly(Vinyliden Fluoride-Trifluoroethylene-Chlorofluoroethylene), Journal of Applied Physics, 97, 094105, pp. 1-4, 2005.
Laxminarayana, et al., Functional Nanotube-Based Textiles: Pathway to Next Generation Fabrics With Enhanced Sensing Capabilities, Textile Res. J., 75(9), 670-680, 2005.
Livingston, et al., A Comparative Study of Biphasic Calcium Phosphate Ceramics for Human Mesenchymal Stem-Cell-Induced Bone Formation, Biomaterials, 26, pp. 3631-3638, 2005.
Montjovent et al., Biocompatibility of Bioresorbable Poly(L-lactic acid) Composite Scaffolds Obtained by Supercritical Gas Foaming With Human Fetal Bone Cells, Tissue Engineering 11, pp. 1640-1649, 2005.
Naber, et al., Low-Voltage Programmable Ferroelectric Polymer Field-Effect Transistors, Applied Physics Letters, 87: 203509, pp. 51-57, 2005.
Shapiro, et al., Oscillating Field Stimulation for Complete Spinal Cord Injury in Humans: A Phase 1 Trial, Journal of Neurosurgery Spine, 2(1):3-10, 2005.
Wutticharoenmongkol, et al., Electrospinning of Polystyrene/Poly(2-methoxy-5-(2'-ethylhexyloxy)-1,4-phenylene Vinylene) Blends, Journal of Polymer Science: Part B: Polymer Physics, vol. 43, pp. 1881-1891, 2005.
Wutticharoenmongkol, Preparation and Characterization of Novel Bone Scaffolds Based on Electrospun Polycaprolactone Fibers Filled with Nanoparticles, Macromolecular Bioscience, vol. 6, pp. 70-77, 2005.
Zhang et al., Tissue-Engineering Approaches for Axonal Guidance, Brain Res. Brain Res. Rev, vol. 49, pp. 48-64, 2005.
Zhao, et al., Preparation and Properties of Electrospun Poly(Vinylidene Fluoride) Membranes, Journal of Applied Polymer Science, vol. 97, 466-474, 2005.
Beloti, et al., In Vitro Biocompatibility of a Novel Membrane of the Composite Poly(Vinylidene-Trifluoroethylene)/Barium Titanate, InterScience Journal of Biomedical Materials Research Part A, 281-288, 2006.
Cizkova, et al., Transplants of Human Mesenchymal Stem Cells Improve Functional Recovery After Spinal Cord Injury in the Rat, Cellular and Molecular Neurobiology, 26(7/8):1167-80, 2006.
Georgiou et al., Polyactic Acid-Phosphate Glass Composite Foams as Scaffolds for Bone Tissue Engineering, J. Biomed. Mat. Res. Part B: Applied Biomaterials, Published Online Jul. 12, 2006.
Himes, et al., Recovery of Function Following Grafting of Human Bone Marrow-Derived Stromal Cells Into the Injured Spinal Cord, Neurorehabilitation and Neural Repair, 20:278-96, 2006.
Hung, et al., The Effect of Chitosan and PVDF Substrates on the Behavior of Embryonic Rat Cerebral Cortical Stem Cells, Biomaterials, 27, 4461-4469, 2006.
Nasir, et al., Control of Diameter, Morphology, and Structure of PVDF Nanofiber Fabricated by Electrospray Deposition, Journal of Polymer Science: Part B: Polymer Physics, vol. 44, 779-786, 2006.

(56) References Cited

OTHER PUBLICATIONS

Oudega, et al., Schwann Cell Transplantation for Repair of the Adult Spinal Cord, Journal of Neurotrauma, 23(3-4), 453-67, 2006.
Rezwan et al., Biodegradable and Bioactive Porous Polymer/inorganic Composite Scaffolds for Bone Tissue Engineering, Biomaterials, 27, pp. 3413-3431, 2006.
Tashiro, et al, Structural Correlation Between Crystal Lattice and Lamellar Morphology in the Ferroelectric Phase Transition of Vinylidene Fluoride-Trifluoroethylene Copolymers as Revealed by the Simultaneous Measurements of Wide-Angle and Small-Angle X-Ray Scatterings, Polymer, 47, 5433-5444, 2006.
Thomas et al., Electrospun Bioactive Nanocomposite Scaffolds of Polycaprolactone and Nanohydroxyapatite for Bone Tissue Engineering, Journal of Nanoscience Nanotechnology, 6(2), pp. 487-493, 2006.
Wu, et al., Poly(Vinylidene Fluoride)/Polyethersulfone Blend Membranes: Effects of Solvent Sort, Polyethersulfone and Polyvinylpyrolidone Concentration on Their Properties and Morphology, Journal of Membrane Science, 285, 290-298, 2006.
Wutticharoenmongkol et al., Preparation and Characterization of Novel Bone Scaffolds Based on Electrospun Polycaprolactone Fibers Filled with Nanoparticles, Macromol. Biosci. 6, pp. 70-77, 2006.
Wutticharoenmongkol, et al., Novel Bone Scaffolds of Electrospun Polycaprolactone Fibers Filled With Nanoparticles, Journal of Nanoscience Nanotechnology, 6(2), pp. 514-522, 2006.
Yang, et al., Preparation of Bioelectret Collagen and Its Influence on Cell Culture In Vitro, J. Mater. Sci: Mater Med, 17:767-771, 2006.
Catalani, et al., Evidence for Molecular Orientation and Residual Charge in the Electrospinning of Poly (Butylenes Terephthalate) Nanofibers, Macromolecules, vol. 40, pp. 1693-7, 2007.
Greiner, et al, Electrospinning: A Fascinating Method for the Preparation of Ultrathin Fibers, Angewandte Chemie Int. Ed. Engl. 46: 5670-5703, 2007.
Huang, Isothermal Crystallization of High-Density Polyethylene and Nanoscale Calcium Carbonate Composites, Journal of Applied Science, 107, pp. 3163-3172, 2007.
Miyazaki, et al., Crystallization Rate of Amorphous Nifedipine Analogues Unrelated to the Glass Transition Temperature, Interational Journal of Pharmaeceutics, 336, pp. 191-195, 2007.
Osiris Therapeutics Announces Positive One Year Data from Chondrogen Trial for Knee Repair, Osiris Therapeutics, Inc., Ref. Type: Internet Communication, 2007.
http://stemcells.nih.gov/info/scireport/appendixE.asp, (visited Dec. 28, 2007; last visited Aug. 25, 2011), 6 pages.
Sun, et al. Crystallization and Thermal Properties of Polyamide 6 Composites Filled With Different Nanofillers, Materials Letters, 61, pp. 3963-3966, 2007.
Venugopal et al., Biocomposite Nanofibres and Osteoblasts for Bone Tissue Engineering, Nanotechnology, 18, pp. 1-8, 2007.
Wi, et al., Characterization of Poly(Vinylidene Fluoride-Trifluoroethylene) 50/50 Copolymer Films as a Gate Dielectric, J. Mater Sci: Mater Electron, pp. 1-6, 2007.
Zhou et al., In Vitro Bone Engineering Based on Polycaprolactone and Polycaprolactone-Tricalcium Phosphate Composites, Polym. Int. 56, pp. 333-342, 2007.
Duffell., et al., Long-Term Intensive Electrically Stimulated Cycling by Spinal Cord-Injured People: Effect on Muscle Properties and Their Relation to Power Output, Muscle and Nerve, 38:1304-11, 2008.
Kim, et al., The Role of Aligned Polymer Fiber-Based Constructs in the Bridging of Long Peripheral Nerve Gaps, Biomaterials, 29(21):3117-27, 2008.
Lankford, et al., Olfactory Ensheathing Cells Exhibit Unique Migratory, Phagocytic and Myelinating Properties in the X-Irradiated Spinal Cord Not Shared by Schwann Cells, Glia, (epub ahead of print), 2008.
PCT International Search Report and Written Opinion dated Jun. 25, 2008 for PCT/US2005/043876.
PCT International Search Report and Written Opinion for PCT/US2008/067322 dated Sep. 29, 2008.
PCT International Search Report dated Dec. 24, 2008 for PCT/US2008/067322.
European Search Report dated Dec. 9, 2009 for PCT/US2005/043876.
PCT International Preliminary Report on Patentability dated Dec. 22, 2009 for PCT/US2008/067322.
PCT International Search Report and Written Opinion for PCT/US2012/050156 dated Feb. 1, 2013.
European Patent Office Action for European Patent Application No. 05852938.9 dated Jul. 1, 2014.
U.S. Appl. No. 14/381,496, filed Aug. 27, 2014.
Hardingham, Proteoglycans: Their Structure, Interactions and Molecular Organization in Cartilage, Biochemical Society Transactions, vol. 9, No. 6, pp. 489-497, 1981.
Davis, et al., Structural and Dielectric Investigation on the Nature of the Transition in a Copolymer of Vinylidene Fluoride and Trifluoroethylene, Macromolecules, 15: 329-333, 1982.
Lovinger, Ferroelectric Polymers, Science, New Series, vol. 220, No. 4602, pp. 1115-1121, 1983.
Patel, et al., Perturbation of the Direction of Neurite Growth by Pulsed and Focal Electric Fields, Journal of Neurosci, vol. 4, pp. 2939-47, 1984.
Humphrey, et al., The Dielectric Piezoelectric and Pyroelectric Properties of VDF-TrFE Copolymers, Plessey Research (Caswell) Limited, Allen Clark Research Centre, Caswell, Towcester, Northants, NN12 8EQ, England, 1986.
Borgens, Electric Fields in Vertebrate Repair, Natural and Applied Voltage in Vertebrate Regeneration and Hearling, Wiley-Liss, 1989.
Sambrook et al., Molecular Cloning: A Laboratory Manual, $2^{nd}$ 3d., Cold Spring Harbor Laboratory, Cold Spring Harbor Laboratory Press, Cold Spring Harbor, NY, 1989. (cover page and Table of Contents for vols. 1-3).
Koga, et al., Crystallization, Field-Induced Phase Transformation, Thermally Induced Phase Transition, and Piezoelectric Activity in P(Vinylidene Fluoride-TrFE) Copolymers with High Molar Content of Vinylidene Fluoride, J. Appl. Phys, 67(2), pp. 965-974, 1990.
Valentini, Electrically Charged Polymeric Substrates Enhance Nerve-Fiber Outgrowth in Vitro, Biomaterials, vol. 13, pp. 183-90, 1992.
Ausubel, et al., Current Protocols in Molecular Biology, John Wiley & Sons, New York, NY, 1993. (cover page and Table of Contentst).
Ohigashi, et al., Formation of "Single Crystalline Films" of Ferroelectric Copolymers of Vinylidene Fluoride and Trifluoroethylene, Appl. Phys. Lett., 66(24), pp. 3281-3283, 1995.
Kapur, et al, Human Monocyte Morphology is Affected by Local Substrate Charge Heterogeneity, J, Biomed Mater. Res., 32: 133, 1996. (abstract only).
Kapur., et al., Fabrication and Selective Surface Modification of 3-Dimensionally Textured Biomedical Polymers from Etched Silicon Substrates, Journal of Biomedical Materials Research, vol. 33, pp. 205-216, 1996.
Bouaziz, et al., Vascular Endothelial Cell Responses to Different Electrically Charged Poly(Vinylidene Fluoride) Supports Under Static and Oscillating Flow Conditions, Biomaterials, vol. 18, No. 2, 107-112, 1997.
Christie, et al., Ferroelectric and Piezoelectric Properties of a Quenched Poly(Vinylidene Fluoride-Trifluoroethylene) Copolymer, Journal of Polymer Science: Part B: Polymer Physics, vol. 35, 2671-2679, 1997.
Furukawa, Structure and Functional Properties of Ferroelectric Polymers, Advances in Colloid and Interface Science, 71-72; 183-208, 1997.
Miraglia, S. "A Novel Five-Transmembrane Hematopoietic Stem Cell Antigen: Isolation, Characterization, and Molecular Cloning," *Blood* 90:5013-21, 1997.
Omote, et al., Temperature Dependence of Elastic, Dielectric, and Piezoelectric Properties of "Single Crystalline" Films of Vinylidene Fluoride Trifluoroethylene Copolymer, J. Appl. Phys., 81(6), pp. 2760-2769, 1997.
Schmidt, et al., Stimulation of Neurite Outgrowth Using an Electrically Conducting Polymer, Proc. Natl. Acad. Sci, vol. 94, pp. 8948-8953, 1997.

(56) References Cited

OTHER PUBLICATIONS

Virts, E. et al. "Murine Mast Cells and Monocytes Express Distinctive Sets of CD45 Isoforms," *Immunology* 34(16-17):1119-97, 1997.
Yin, A.H. "AC133, A Novel Marker for Human Hematopoietic Stem and Progenitor Cells," *Blood* 90:5002-12, 1997.
Bune, et al., Two-Dimensional Ferroelectric Films, Nature, vol. 391, 874-877, 1998.
Zhao, et al., Electromechanical Properties of Electrostrictive Poly(Vinylidene Fluoride-Trifluoroethylene) Copolymer, Applied Physics Letters, vol. 73, No. 14, pp. 2054-2056, 1998.
Borgens, Electrically Mediated Regeneration and Guidance of Adult Mammalian Spinal Axons into Polymeric Channels, Neuroscience, 91(1):251-64; 1999.
Laurencin, C.T. "Tissue Engineering: Orthopedic Applications," *Ann. Rev. Biomed. Eng'g* 1:19-46, 1999.
Sittinger et al., Joint cartilage regeneration by tissue engineering, Z. Rheumatol, 58:130-5, 1999.
Hilczer, et al., The Method of Matching Resonance Frequencies in Coupled Transmitter PVDF/TRFE Diaphragms, IEEE Transactions on Dielectrics and Electrical Insulation, vol. 7, No. 4, pp. 498-502, 2000.
Ponticello et al., Gelatin-Based Resorbable Sponge As a Carrier Matrix for Human Mesenchymal Stem Cells in Cartilage Regeneration Therapy, *J Biomed Materials Res* 52: 246-255, 2000.
Brook et al., Columns of Schwann Cells Extruded Into the CNS Induce In-Growth of Astrocytes to Form Organized New Glial Pathways, GLIA, 33:118-130, 2001.
Guo et al., Biological features of mesenchymal stem cells from human bone marrow, Chinese Med J.. 114:950-3, 2001.
Harrison, et al., Piezoelectric Polymers, ICASE, NASA Langley Research Center, Hampton, Virginia, NASA/CR-2001-211422, ICASE Report No. 2001-43, pp. 1-26, 2001.
Koombhongse, et al., Flat Polymer Ribbons and Other Shapes by Electrospinning, Journal of Polymer Science: Part B: Polymer Physics, vol. 39, 2598-2606, 2001.
Kotwal, et al., Electrical Stimulation Alters Protein Adsorption and Nerve Cell Interactions With Electrically Conducting Biomaterials, Biomaterials, 22: 1055-1064, 2001.
N.S.C.I.A., Spinal Cord Injury Fact Sheet, Birmingham, 2001; http://users.erols.com/nscia/resource/factshts/.
Negishi, Optic Nerve Regeneration Within Artificial Schwann Cell Graft in the Adult Rat, Brain Research Bulletin, 55:409-419, 2001.
Ploss, et al., Poling Study of PZT/P(VDF-TrFE) Composites, Composites Science and Technology, 61, 957-962, 2001.
Rahman et al., Enhancement of Chondrogenic Differentiation of Human Articular Chondrocytes by Biodegradable Polymers, Tissue Engineering, 7:781-90, 2001.
Yannas IV, Tissue and Organ Regeneration in Adults, Springer, 2001. (cover page and Table of Contents).
Li et al., Electrospun Naofibrous Structure: A Novel Scaffold for Tissue Engineering, Journal of Biomedical Materials Research, vol. 60, No. 4, pp. 613-621, 2002.
Benz, et al., Determination of the Crystalline Phases of Poly(Vinylidene Fluoride) Under Different Preparation Conditions Using Differential Scanning Calorimetry and Infrared Spectroscopy, Journal of Applied Polymer Science, vol. 89, 1093-1100, 2003.
Li, et al., Biological Response of Chondrocytes Cultured in Three-Dimensional Nanofibrous Poly($\epsilon$--caprolactone) Scaffolds, J. Biomed. Mat. Res. Part A., 67A, 4, pp. 1105-1114, 2003.
Livingston, et al., Mesenchymal Stem Cells Combined With Biphasic Calcium Phosphate Ceramics Promote Bone Regeneration, Journal of Materials Science: Materials in Medicine, 14: 211-218, 2003.
Luu et al., "Development of a Nanostructured DNA Delivery Scaffold via Electrospinning of PLGA and PLA-PEG block copolymers". Journal of Controlled Release, vol. 89, pp. 341-353, 2003.
Murphy et al., Stem Cell Therapy in a Caprine Model of Osteoarthritis, *Arthritis Rheumatism* 48: No. 12, 3464-3474, 2003.
Sachlos, et al., Making Tissue Engineering Scaffolds Work, Review of the Application of Solid Freeform Fabrication Technology to the Production of Tissue Engineering Scaffolds, *European Cells & Materials* 5: 29-40, 2003.
Seoul, et al., Electrospinning of Poly(Vinylidene Fluoride)/Dimethylformamide Solutions With Carbon Nanotubes, Journal of Polymer Science: part B: Polymer Physics, vol. 41, 1572-1577, 2003.
Sikavitsas et al., "Mineralized Matrix Deposition by Marrow Stromal Osteoblasts in 3D Perfusion Culture Increases With Increasing Fluid Shear Forces". PNAS, vol. 100, No. 25, pp. 14683-14688, Dec. 9, 2003.
Wan-Ju, et al., Biological Response of Chondrocytes Cultrued in Three-Dimensional Nanofibrous Poly($\epsilon$--caprolactone) Scaffolds, J. Biomed. Mater. Res. 67A:1105-1114, 2003.
Yeh, E.T.H. et al., "Transdifferentiation of Human Peripheral Blood CD34+-Enriched Cell Population Into Cardiomyocytes, Endothelial Cells, and Smooth Muscle Cells in Vivo," Circulation 108:2070-73, 2003.
Yoshimoto et al., A Biodegradable Nanofiber Scaffold by Electrospinning and its Potential for Bone Tissue Engineering, Biomaterials, 24, pp. 2077-2082, 2003.
Zong et al., Electrospun Non-woven Membranes As Scaffolds for Heart Tissue Constructs. 226$^{th}$ ACS National Meeting, 2003.
Bhattarai, et al., Novel Biodegradable Electrospun Membrane: Scaffold for Tissue Engineering, Biomaterials, vol. 25, No. 13, pp. 2595-2602, 2004.
Bryan, et al., Enhanced Peripheral Nerve Regeneration Through a Poled Bioresorbable Poly(Lactic-co-glycolic Acid) Guidance Channel, J. Neural Eng., 1, 91-98, 2004.
Dezawa, Specific Induction of Neuronal Cells From Bone Marrow Stromal Cells and Application for Autologous Transplantation, Journal of Clinical Investigation; 113:1701-1710, 2004.
Jin et al., "Human Bone Marrow Stromal Cell Responses On Electrospun Silk Fibroin Mats", Biomaterials, vol. 25, pp. 1039-1047, 2004.
Li et al., Carbon Nanotubes Induced Nonisothermal Crystallization of Ethylene-Vinyl Acetate Copolymer, Materials Letter, 58, pp. 3967-3970, 2004.

\* cited by examiner

SYSTEM AND METHOD FOR A HYDROGEL AND HYDROGEL COMPOSITE FOR CARTILAGE REPAIR APPLICATIONS

CROSS REFERENCE TO RELATED APPLICATIONS

This application claims the benefit of U.S. Provisional Application No. 61/159,747, titled "System and Method for a Hydrogel and Hydrogel composite for Cartilage Repair Applications," filed Mar. 12, 2009, which is incorporated herein by reference in its entirety.

FIELD OF THE INVENTION

This invention relates to the fields of biotechnology, and regenerative medicine. More specifically, it relates to scaffolding, cell scaffolding, and cartilage repair.

BACKGROUND

Articular cartilage has a limited intrinsic ability to heal. For this reason, orthopaedic management of these lesions remains a persistent problem for the orthopedist and patient. The importance of treating injury to articular cartilage is underscored by the fact that several million people are affected in the United States alone by cartilage damage. (See Praemer A, Furner S. Rice D P. Musculoskeletal conditions in the United States: American Academy of Orthopaedic Surgeons; 1999 p. 34-9). Focal lesions of articular cartilage can progress to more widespread cartilage destruction and arthritis that is disabling. Thus, numerous procedures have been developed in an attempt to treat these lesions and halt or slow the progression to diffuse arthritic changes. (See Browne J E, Branch T P. Surgical alternatives for treatment of articular cartilage lesions. J Am Acad Orthop Surg 2000; 8(3):180-9). Surgical procedures to restore articular cartilage include marrow stimulation techniques, autologous chondrocyte transplant (See Browne J E, Anderson A F, Arciero R, Mandelbaum B, Moseley J B, Micheli L J, et al. Clinical outcome of autologous chondrocyte implantation at 5 years in US subjects. Clinical Orthopaedics and Related Research 2005; 436: 237-45), and osteoarticular transfer (See Magnussen R A, Dunn W R, Carey J L, Spindler K P. Treatment of focal articular cartilage defects in the knee: a systematic review. Clinical Orthopaedics and Related Research 2008; 466(4): 952-62). At present, none of these techniques have been able to restore a normal cartilaginous surface and have suffered from poor integration with the surrounding normal articular cartilage. Frequently, the repair tissue has inferior biochemical and biomechanical properties. The tissue engineering concepts described herein may eliminate many of the problems associated with the current surgical options.

An alternative cell source demonstrating promise for cartilage repair is the adult stem cell. Mesenchymal stem cells (MSCs) are multipotent cells that are capable of differentiating along several lineage pathways. (See Pittenger M F, Mackay A M, Beck S C, Jaiswal R K, Douglas R, Mosca J D, et al. Multilineage potential of adult human mesenchymal stem cells. Science 1999; 284:143-7). From a small bone marrow aspirate obtained from adults, MSCs can be isolated and expanded into billions of cells due to their proliferative capacity. (See Friedenstein A, Chailakhyan R, Gerasimov U V. Bone Marrow Osteogenic Stem Cells: In Vitro Cultivation and Transplantation in Diffusion Chambers. Cell Tissue Kinet 1987; 20(3):263-72). Additional characterization has also identified a panel of immunophenotypic and cell surface markers characteristic of the MSC. (See Haynesworth S, Baber M, Caplan A. Cell Surface Antigens on Human Marrow-Derived Mesenchymal Stem Cells are Detected by Monoclonal Antibodies. J Cell Physiol 1992; 138:8-16).

In vitro and in vivo analyses have demonstrated that culture expanded MSCs can differentiate into osteoblasts, chondrocytes, adipocytes, tenocytes, myoblasts, and neural cell lineages. MSC populations that had been taken out to 15 passages as well as cyropreserved still have the capacity to differentiate and proliferate, suggesting that MSCs may be valuable as a readily available and abundant source of cells in the tissue engineering field. (See Jaiswal N, Haynesworth S E, Caplan A I, Bruder S P. Osteogenic differentiation of purified culture-expanded human mesenchymal stem cells in vitro. J Cell Biochem 1997; 64:295-312; See also Kadiyala S, Jaiswal N, Bruder S P. Culture-expanded, bone marrow-derived mesenchymal stem cells can regenerate a critical-sized segmental bone defect. Tissue Engineering 1997; 3(2):173-85; See also Rickard D J, Sullivan T A, Shenker B J, Leboy P S, Kazhdan I. Induction of rapid osteoblast differentiation in rat bone marrow stromal cell cultures by dexamethason and BMP-2. Dev Bio 1994; 161:218-28). Furthermore, recent studies have demonstrated that the use of allogeneic MSCs can successfully repair bone and other tissue types in various animal models without provoking an adverse immune response. (See Livingston T L, Peter S P, Archambault M, Van Den Bos C, Gorden S, Kraus K, et al. Allogeneic stem cells regenerate a critically-sized canine segmental gap. Journal of Bone and Joint Surgery American 2003; 85-A(10):1927-35; See also Chamberlain G, Fox J, Ashton B, Middleton J. Concise review: mesenchymal stem cells: their phenotype, differentiation capacity, immunological features, and potential for homing. Stem Cells 2007; 25(11):2739-49). An allogeneic MSC approach provides an off-the-shelf therapy, where allogeneic MSCs are used as universal cells and in turn, provide cells to a much larger clinical population. They are also currently in clinical trials for various disorders or conditions, including cartilage repair, as an allogeneic cell source.

In recent clinical trial results, 30% of patients receiving direct injection of MSCs demonstrated improvement in cartilage and joint condition. (See Chondrogen clinical trial information for the treatment of knee injuries. Osiris Therapeutics, Inc. 2008). Concerns, however, are the long term efficacy of MSCs for cartilage repair. It has been well documented that MSCs during chondrogenesis exhibit mixed phenotypes as opposed to the hyaline phenotype typically displayed by chondrocytes. (See Karlsson C, Brantsing C, Svensson T, Brisby H, Asp J, Tallheden T, et al. Differentiation of human mesenchymal stem cells and articular chondrocytes: analysis of chondrogenic potential and expression pattern of differentiation-related transcription factors. Journal of Orthopaedic Research 2007; 25:152-63). In culture, it has also been reported that MSCs during chondrogenesis express chondrocyte hypertrophy-associated genes, including type X collagen, alkaline phosphatase, matrix metalloproteinase 13, vascular endothelial growth factor (VEGF), and parathyroid hormone-related protein receptor (PTHrPR). (See Mueller M B, Tuan R S. Functional characterization of hypertrophy in chondrogenesis of human mesenchymal stem cells. Arthritis and Rheumatism 2008; 58(5):1377-88). This suggests that MSCs undergoing chondrogenic differentiation may proceed toward the chondrocyte hypertrophy stage, which is typical of endochondral ossification during skeletal development.

Moreover, in in vivo ectopic studies, human MSCs undergoing chondrogenesis can exhibit chondrocyte hypertrophy (typically seen in osteoarthritis) leading to vascular invasion and mineralization. (See Pelttari K, Winter A, Steck E, Goetzke K, Hennig T, Ochs B G. Premature induction of hypertrophy during in vitro chondrogenesis of human mesenchymal stem cells correlates with calcification and vascular invasion after ectopic transplantation in SCID mice. Arthritis and Rheumatism 2006; 54:3254-66). This phenomenon is thus a concern for the clinical application of MSCs in articular cartilage repair, because chondrocyte hypertrophy in neocartilage could ultimately lead to apoptosis, vascular invasion, and ossification, as observed in the cartilage growth plate.

In the body, adult stem cells are often localized to specific chemically and topologically complex microenvironments, or so-called "niches". Increasing experimental evidence supports the notion that stem cells can adjust their properties according to their surroundings, and select specific lineages according to the cues they receive from their niche. (See Xie L, Spradling A C. A niche maintaining germ line stem cells in the Drosophila ovary. Science 2000; 290(5490):328; See also Fuchs E, Segre J. Stem cells: a new lease on life. Cell 2000; 100:143-55; See also Watt F M, Hogan B L M. Out of eden: stem cells and their niches. Science 2000; 287(5457):1427). To maximize successful stem cell therapy in the repair of a specific tissue type, the microenvironment of the cells should be designed to relay the appropriate chemical and physical signals to them. Mimicking characteristics of the microenvironment during cartilage development is a viable approach. During cartilage development, one of the earliest events is pre-cartilage mesenchymal cell aggregation and condensation resulting from cell-cell interaction, which is mediated by both cell-cell (neural cadherin and neural cell adhesion molecule) and cell-matrix adhesion (fibronectin, proteoglycans, hyaluronic acid and collagens). (See DeLise A M, Fischer L, Tuan R S. Cellular interactions and signaling in cartilage development. Osteoarthritis and Cartilage 2000; 8:309-34). Type I collagen being the predominant matrix protein present in the early stages of development is later transformed to Type II collagen by increased cell synthesis during differentiation. (See Safronova E E, Borisova N V, Mezentseva S V, Krasnopol'skaya K D. Characteristics of the macromolecular components of the extracellular matrix in human hyaline cartilage at different stages of ontogenesis. Biomedical Science 1991; 2:162-8). Multiple growth factors and morphogens such as Wnts, transforming growth factor-beta, and fibroblast growth factors may also be present to support, promote and/or contribute to the regulation of the differentiation process. The present invention extends these findings by, in part, combining MSCs at relatively high cell densities with scaffolds that provide appropriate cues similar to the native extracellular matrix during development.

One way for a biodegradable scaffold to be successful is to make the material's rate of degradation commeserate with the growth of new cartilage and related tissue. Ideally, the scaffold degrades at a rate to substantially maintain structural support during the initial stages of cartilage formation, but also allows space for continuous growth of new cartilage and related tissue.

It is therefore of great importance to develop a scaffold that will overcome these issues and provide the appropriate cues to support chondrogenesis of the stem cells, e.g., MSCs.

SUMMARY

In certain aspects, the present invention provides compositions and methods of preparing a hydrogel, as well as preparing a three-dimensional matrix of micron and/or nano-sized electrospun fibers, wherein the electrospun fibers are formed from a electrospun composite comprising a water soluble cellulose compound. The matrix provides a scaffold supporting and promoting cartilage growth, differentiation, and/or regeneration and repair.

Additionally, the present invention provides novel hydrogel and scaffolds that closely mimic the natural extracellular matrix (ECM) of cartilage. These hydrogels and scaffolds, when combined with stem/progenitor cells, can support and promote stem cell chondrogenesis. In one embodiment of this aspect, the present invention utilizes sodium cellulose sulfate (NaCS) as a scaffold material for use in cartilage tissue repair. NaCS can form a cross-linked hydrogel for use as an injectable delivery system for use alone or in combination with other components, such as cells, growth factors, polysaccharides or combinations thereof. In an additional embodiment, the hydrogel can also be used in combination with a fibrous mesh as a scaffold construct that more closely mimics the natural ECM of cartilage in both structure and function.

In another aspect, the present invention provides a hydrogel for use in tissue engineering or an implantable material comprising at least two water soluble cellulose compounds, wherein the compounds are crosslinked. The compounds may be crosslinked, for example, by means of ionic interactions. In certain embodiments, at least one of the water soluble cellulose compounds is a sodium cellulose sulfate compound.

In certain aspects, the hydrogel may further comprise a fibrous network. For example, in one embodiment of this aspect the fibrous network comprises at least one polymer selected from the group consisting of a nondegradable polymer and a degradable polymer. In certain embodiments, the nondegradable polymer is selected from the group consisting of a polyurethane, a polyvinylidine fluoride, and a polyvinylidine fluoride trifluoroethylene. In other embodiments, the degradable polymer is selected from the group consisting of a poly(lactic acid-glycolic acid), a poly(lactic acid), a poly (glycolic acid), a poly(orthoester), a poly(phosphazene), poly (or polycaprolactone, a polyamide, a polysaccharide, and a collagen. In a preferred embodiment, the polymer is poly (lactic acid-glycolic acid).

In additional aspects, the hydrogel may further comprise a stem cell or progenitor cell, for example, a mesenchymal stem cell isolaged from a subject, e.g., a mammal such as a human. The hydrogel embedded with stem cells promotes stem cell chrondrogenesis. The hydrogel may also further comprise collagen, growth factor, or non-functional soluble polysaccharides, or combinations thereof. In a preferred embodiment, the polysaccharide is dextran.

In another aspect, the present invention relates to an implantable scaffold for use in tissue engineering or as an implantable material comprising a three-dimensional matrix of micron- and/or nano-sized electrospun fibers, wherein the electrospun fibers are formed from an electrospun composite comprising a water soluble cellulose compound. In certain embodiments, the fibers are micron sized, and/or the three dimensional matrix of electrospun fibers comprises micron-sized pores.

In another aspect, the present invention relates to a method for preparing an implantable three-dimensional matrix of micron sized electrospun fibers comprising an electrospun composite containing a water soluble cellulose compound.

In another aspect, the present invention relates to a method of preparing a hydrogel to facilitate cartilage repair, the method comprising the steps preparing a composite comprising a water soluble cellulose compound; electrospinning the composite; and forming a three-dimensional non-woven matrix of electrospun fibers comprising the composite. In certain embodiments, the hydrogel may further comprise a fibrous network. In additional embodiments, the fibrous network may comprise at least one polymer selected from the group consisting of a nondegradable polymer and a degradable polymer. Preferably, the electrospun fibers are micron sized and the matrix of electrospun fibers comprise micron-sized pores. The method may further comprise the steps seeding the three-dimensional nonwoven matrix of electrospun fibers with isolated differentiable human mesenchymal cells; and growing the differentiable human mesenchymal cells on the three-dimensional nonwoven matrix of electrospun fibers so that the differentiable human mesenchymal cells differentiate into a mature cell phenotype on the hydrogel.

In another aspect, the present invention relates to methods of treating arthritis and treating or repairing cartilage tissue in a subject in need of such repair, the method comprising administering to said subject an effective amount of a hydrogel or scaffold as described herein.

The preceding general areas of utility are given by way of example only and are not intended to be limiting on the scope of the present disclosure and appended claims. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional objects and advantages are expressly included within the scope of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

DETAILED DESCRIPTION

Figure 1:
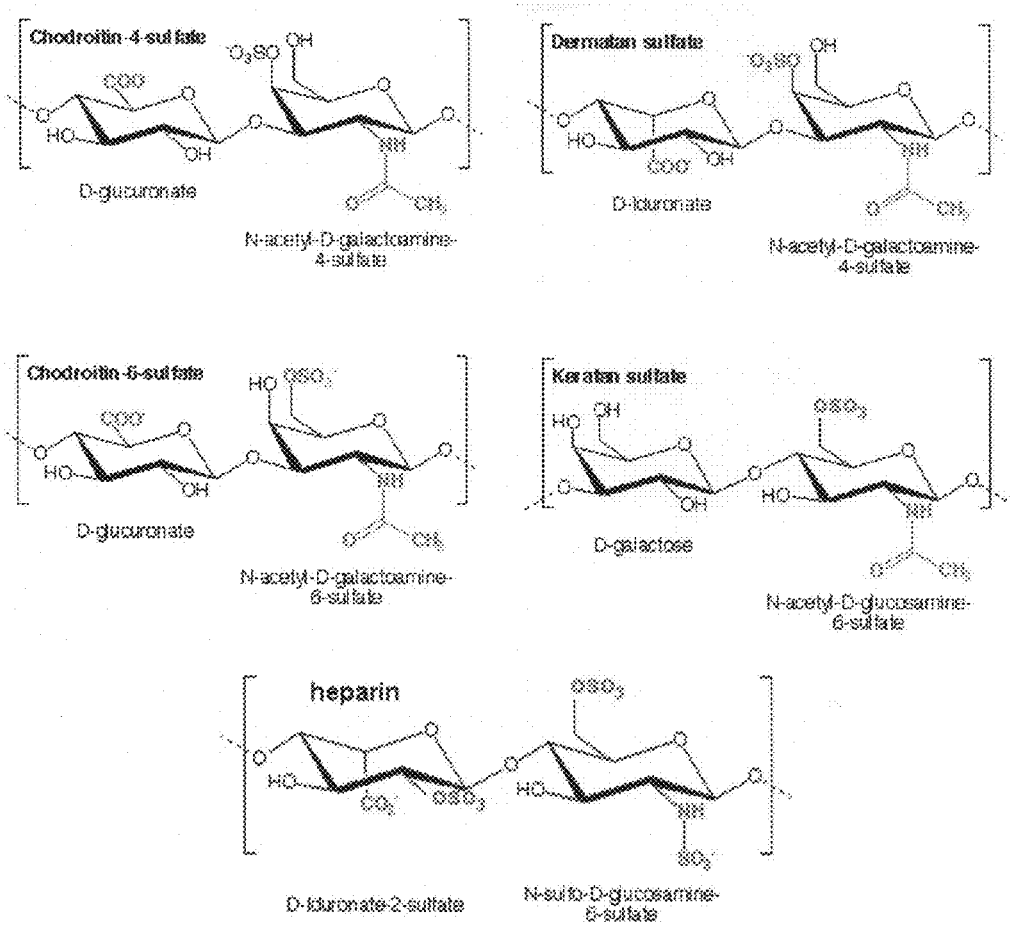
FIG. 1 shows the structure of several glycosaminoglycans.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

The present invention provides a hydrogel comprising a water soluble cellulose compound. The invention also provides an electrospun scaffold of water soluble cellulose material having micron sized fiber diameters and pores and a method of preparing such scaffolds. The pore size diameters of the micron sized fibers in the scaffold provide for improved cell infiltration, aggregation, and tissue formation throughout the scaffold when compared with nanosized fibers. Additionally, the present invention provides novel hydrogel and scaffolds that closely mimic the natural extracellular matrix (ECM) of cartilage. These hydrogels and scaffolds, when combined with stem/progenitor cells, can support and promote stem cell chondrogenesis.

As used herein, the terms "bioactive" and "bioactivity" are used interchangeably to refer to any effect on, interaction with, or response from living tissue.

As used herein, the term "biocompatible material" refers to a material that the body generally accepts without a major immune response, which is capable of implantation in biological systems, for example, tissue implantation, without causing excessive fibrosis or rejection reactions. As used herein, the term "biodegradable" refers to the ability of a substance or material to break down into harmless substances by the action of living organisms.

As used herein, the term "water soluble cellulose compounds" refers to a family of cellulose compounds that are long chain macromolecules of repeating glucose units substituted to varying extents with anionic sulfate groups, which can be represented as —$SO_3^-$. Molecular weights of water soluble cellulose compounds encompassed by the invention typically range from about $5 \times 10^5$ to about $3 \times 10^6$ g/mol. The hydroxyl groups of each glucose unit can be substituted with from one to three sulfate groups. The sulfonation imparts water solubility to the otherwise insoluble cellulose. The availability of unsubstituted hydroxyl groups provides reactive sites for crosslinking for the soluble cellulose sulfate. The negative charge of the sulfate group is balanced by the positive charge of a cationic species, typically an alkali metal cation, and preferably the sodium cation.

As used herein, the term "collagen" refers to any of a family of extracellular, closely related proteins occurring as a major component of connective tissue, giving it strength and flexibility. At least 14 types exist, each composed of tropocollagen units that share a common triple-helical shape but that vary somewhat in composition between types, with the types being localized to different tissues, stages, or functions. In some types, including the most common, Type I, the tropocollagen rods associate to form fibrils or fibers; in other types the rods are not fibrillar but are associated with fibrillar collagens, while in others they form nonfibrillar, nonperiodic but structured networks. Tropocollagen, the basic structural unit of collagen comprises a helical structure consisting of three polypeptide chains, each chain composed of about a thousand amino acids, coiled around each other to form a spiral and stabilized by inter- and intrachain covalent bonds. It is rich in glycine, which occurs as nearly one residue out of three, as well as proline, hydroxyproline, and hydroxylysine; the last two rarely occur in other proteins.

As used herein, the terms "microscale fiber" or "micron sized fiber" are used interchangeably to refer to fibers whose diameter ranges from about 1 micrometer ($10^{-6}$ m) to about 1000 micrometers. The terms "nanoscale fiber" or "nano sized fiber" are used interchangeably to refer to fibers whose diameter ranges from about 1 nanometer ($10^{-9}$ m) to about 1000 nanometers.

As used herein, the term "polymer" as used herein refers to a macromolecule formed by the chemical union of five or more identical combining units called monomers. In most cases, the number of monomer is quite large and often is not precisely known. In synthetic polymers, this number may be controlled to a predetermined extent. Combinations two, three, or four monomers are called, respectively, dimers, trimers, and tetramers, and are known collectively as oligomers. Polymers may be inorganic (e.g., siloxane, sulfur chains, black phosphorus, boron-nitrogen, silicones) or organic (meaning containing carbon). Organic polymers may be natural [e.g., polysaccharides, such as starch, cellulose, pectin, seaweed gums, vegetable gums; polypeptides, such as casein, albumin, globulin, keratin, insulin, DNA; and hydrocarbons], synthetic [such as thermoplastics (unvulcanized elastomers, nylon, polyvinyl chloride, linear polyethylene, polystyrene, polypropylene, polyurethane, acrylate resins); thermosetting (e.g., vulcanized elastomers, crosslinked polyethylene, phenolics, alkyds, polyesters), and semisynthetic (e.g., cellulosics, such as rayon, methylcellulose, cellulose acetate; and modified starches)].

As used herein, the term "homopolymer" refers to a natural or synthetic polymer derived from a single monomer.

As used herein, the terms "poly(glycolic acid)", polyglycolide, and "PGA" are used interchangeably herein to refer to a biodegradable, thermoplastic polymer and the simplest linear, aliphatic polyester. PGA may be obtained commercially, for example, from Sigma-Aldrich.

A "polylactide" is a biodegradable polymer derived from lactic acid. Poly(lactide) or PLA exists in two stereo forms, signified by a D or L for dexorotary or levorotary, or by DL for the racemic mix. The term "PLLA" refers to the biodegradable aliphatic polyester homopolymer poly L-lactic acid. PLLA may be obtained commercially, for example, from Alkermes, Inc.

The terms poly (lactic acid-glycolic acid), poly (D,L-lactide-c-glycoside), and PLGA are used interchangeably to refer to a copolymer of polylactic acid and glycolic acid. PLGA may be obtained commercially, for example, from Alkermes, Inc.

As used herein, the term "polysaccharide" is a long-chain natural or synthetic polymer made up of linked simple sugars (monosaccharides) such as glucose and closely related molecules. Two monosaccharide molecules may be joined by a glycosidic bond to form a disaccharide, as, for instance, in the linkage of glucose and fructose to create sucrose. More complicated polysaccharides such as starch, glycogen, cellulose or chitin consist of numerous monosaccharide units joined by glycosidic bonds.

As used herein, the term "porous" as used herein relates to having minute openings, pores, or holes that may be filled (permeated) by water, air or other materials.

As used herein, the term "stem cells" refers to undifferentiated cells having high proliferative potential with the ability to self-renew that may migrate to areas of injury and may generate daughter cells that may undergo terminal differentiation into more than one distinct cell phenotype. These cells have the ability to differentiate into various cells types and thus promote the regeneration or repair of a diseased or damaged tissue of interest. The term "cellular differentiation" refers to the process by which cells acquire a cell type. The term "progenitor cell" as used herein refers to an immature cell in the bone marrow that may be isolated by growing suspensions of marrow cells in culture dishes with added growth factors. Progenitor cells are referred to as colony-forming units (CFU) or colony-forming cells (CFC). The specific lineage of a progenitor cell is indicated by a suffix, such as, but not limited to, CFU-F (fibroblastic).

As used herein, the terms "osteoprogenitor cells", "mesenchymal cells", "mesenchymal stem cells (MSC)", or "marrow stromal cells" are used interchangeably to refer to multipotent stem cells that differentiate from CFU-F cells capable of differentiating along several lineage pathways into osteoblasts, chondrocytes, myocytes and adipocytes. When referring to bone or cartilage, MSCs commonly are known as osteochondrogenic, osteogenic, chondrogenic, or osteoprogenitor cells, since a single MSC has shown the ability to differentiate into chondrocytes or osteoblasts, depending on the medium.

As used herein, the term "chondrocytes" as used herein refers to cells found in cartilage that produce and maintain the cartilaginous matrix. From least to terminally differentiated, the chondrocytic lineage is (i) Colony-forming unit-fibroblast (CFU-F); (ii) mesenchymal stem cell/marrow stromal cell (MSC); (3) chondrocyte. The term "chondrogenesis" refers to the formation of new cartilage from cartilage forming or chondrocompetent cells.

It must be noted that as used herein and in the appended claims, the singular forms "a", "and", and "the" include plural references unless the context clearly dictates otherwise. All technical and scientific terms used herein have the same meaning. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The principal structural elements of hyaline cartilage are collagen fibers embedded in a stiff hydrogel matrix consisting of water and proteoglycans. The proteoglycans comprises glycosaminoglycans, the majority of which, e.g. 80%-90%, are chondroitin 4- and 6-sulfates. Cellulose sulfate, a monosaccharide polymer of 6-sulfonated glucose, has structural similarity to chondroitin sulfate. Moreover, cellulose sulfate compounds can be synthesized on a commercial scale, and have an enormous advantage in cost and availability over other glycosaminoglycans. Thus, in any of the hydrogel embodiments described herein, sodium cellulose sulfate (NaCS) may be utilized as a scaffold material for use in cartilage tissue repair. NaCS can form a cross-linked hydrogel for use as an injectable delivery system for use alone or in combination with other components, such as cells, growth factors (e.g., cytokines and chemokines), polysaccharides or combinations thereof. The hydrogel can also be used in combination with a fibrous mesh as a scaffold construct that more closely mimics the natural ECM of cartilage in both structure and function.

Incorporation of water soluble cellulose compounds, in particular NaCS, into a scaffold construct either alone or in combination with a fibrous network may require the manipulation of the physical behavior of this material. For Example, in one embodiment, the use of NaCS for use as a hydrogel scaffold without a fibrous network, NaCS is preferably cross-linked to form a more stable gel. In one embodiment, ionic crosslinking is used to crosslink NaCS to form the more stable gel. In embodiments related to NaCS hydrogel in combination with a fibrous network, the NaCS may be crosslinked onto the fibers. As such, the present invention provides compositions and methods for coating poly L-lactic acid (PLLA) electrospun mats with a crosslinked NaCS to produce constructs for cell growth experiments.

NaCS is structurally similar to glycosaminoglycans such as the chondroitin sulfates, dermatan sulfate, keratin sulfate and heparin. Based on these structural similarities, NaCS may impart functional qualities that are similar to the functions of the glycosaminoglycans. It has been observed that receptor binding of growth factors is regulated by the interactions with sulfated glycosaminoglycans. (See Forsten-Williams K, Chu C L, Fannon M, Buczek-Thomas J A, Nugent M A. Control of growth factor networks by heparan sulfate proteoglycans. Annals of Biomedical Engineering 2008; 36(12):2134-48).

Thus present invention also relates to the use of NaCS either used alone or with a fibrous network to provide support for, direct or a combination of both, stem cell chondrogenesis.

NaCS is a negatively charged polyion with more than one negative charge per glucose residue. This structure allows for NaCS to be crosslinked by means of ionic interactions. The advantages of ionic crosslinking are mild preparation conditions and simple procedures, however, any crosslinking technique and bond type may be used. (See Liu Z, Jiao Y, Wang Y, Zhou C, Zhang Z. Polysaccharides-based nanoparticles as drug delivery systems. Advanced Drug Delivery Reviews 2008; 60(15):1650-62). While any material known to one skilled in the art that enables ionic crosslinking may be used, bivalent cations are preferred. For example, calcium ion crosslinking of negatively charged polysaccharides can be utilized to produced nanoparticles for delivery systems. Specifically, Ca-crosslinked alginate nanoparticles have been effectively used to encapsulate protein encoding plasmids. (See You J O, Peng C A. Calcium-alginate nanoparticles formed by reverse microemulsion as gene carriers. Macromolecular Symposia 2004; 219(147):153).

There are two principal structural features of the ECM: a nano-fibrous network or framework composed of protein filaments to which cells can attach, and a hydrated, gel-like medium supported by this network through which soluble nutrients can diffuse. One approach to the development of a viable scaffold that mimics the ECM is engineering both these structural elements into a tissue scaffold construct. In the natural ECM, the hydrogel component has the structural role of mediating compressive stress. The hydrogel consistency is maintained by proteoglycans, which are composed of glycosaminoglycans. These glycosaminoglycans impart a functional aspect to the hydrogel. The functional role of glycosaminoglycans in the extracellular matrix is to complex and sequester specific proteins such as growth factors. Further, the sequestered protein along with the GAG forms a triad complex with a tyrosine kinase receptor at the plasma membrane of the cell to initiate cells response to the presence of the growth factor. (See Forsten-Williams). FIG. 1 shows the structure of several glycosaminoglycans.

Figure 2:
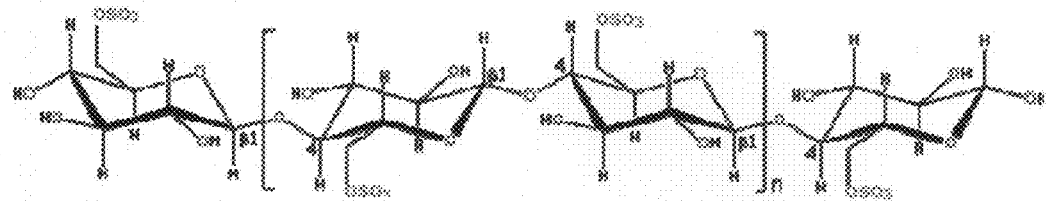
FIG. 2 shows a exemplary structure of a sodium cellulose sulfate compound.

Typical synthetic hydrogels lack functional sites that would enable interaction with proteins present in the media of cell growth cultures or the in vivo milieu. The structure of glycosaminoglycans suggests that the presence of sulfate groups provide that functionality. Receptor binding of growth factors is regulated by the interactions with sulfated glycosaminoglycans. (See Forsten-Williams). Recent reports have suggested that the specific patterns of sulfation function as molecular recognition motifs that can only act with specific growth factors to mediate the cellular processes. (See Gama C L, Tully S E, Sotogaku N, Clark P M, Rawat M, Vaidehi N. Sulfation patterns of glycosaminoglycans encode molecular recognition and activity. Nature Chemical Biology 2006; 2(9):467-73). Similar behavior has yet to be reported for cellulose sulfate. Only functionalized dextran hydrogels containing sulfate groups have been reported, but only for the enhancement of osteoinductive potential of BMP. (See Maire M, Logeart-Avramoglou D, Degat M C, Chaubet F. Retention of transforming growth factor using functionalized dextran-based hydrogels. Biomaterials 2005; 26(14):1771-80). FIG. 2 shows the structure of a regular 6-substituted sodium cellulose sulfate (NaCS).

Water soluble cellulose compounds, particularly NaCS, are known to be biocompatible and have low immunogenicity. These compounds are also biodegradable by hydrolysis into smaller polysaccharides or glucose units. Thus, in another aspect, the present invention provides a transplantable or implantable three-dimensional matrix that is relatively non-immunogenic comprising NaCS.

NaCS differs from native cellulose in that NaCS is soluble in water and aqueous alkali solutions. (See Anderson R A, Feathergill K A, Diao X-H, Cooper M D, Kirkpatrick R, Herold B C, et al. Preclinical evaluation of sodium cellulose sulfate (Ushercell) as a contraceptive antimicrobial agent. Journal of Andrology 2002; 23(3):426-38). NaCS has been shown to be an effective non-toxic, microbicidal agent that is effective against a variety of sexually transmitted diseases. (See Christensen N D, Reed C A, Culp T D, Hermonat P L, Howett M K, Anderson R A. Papillomavirus microbicidal activities of high-molecular-weight cellulose sulfate, dextran sulfate, and polystyrene sulfonate. Antimicrobial Agents and Chemotherapy 2001; 45(12):3427-32). NaCS has also been successfully evaluated as an encapsulate material for the xenotransplantation of porcine islet cells (See Schaffellner S, Stadlbauer V, Stiegler P, Hauser O, Halwachs G, Lackner C. Porcine islet cells microencapsulated in sodium cellulose sulfate. Transplantation Proceedings 2005; 37(1):248-52), and it has also been used in the cryopreservation of islet cells. (See Stiegler P B, Stadlbauer V, Schaffellner S, Halwachs G, Lackner C, Hauser O. Cryopreservation of insulin-producing cells microencapsulated in sodium cellulose sulfate. Transplantation Proceedings 2006; 38(9):3026-30).

Moreover, water soluble cellulose material can be synthesized on a commercial scale. They have an enormous advantage in cost and availability over other glycosaminoglycans that have to be isolated from animal sources or produced by biotechnology processes. For example, heparin sulfate can be purchased for a price of approximately $100 per milligram, while NaCS is available for $1/100^{th}$ the cost. The present invention is the first use of NaCS as a hydrogel material as a tissue/tissue engineering scaffold, and in particular for cartilage regeneration. In certain embodiments, NaCS may be used in injectable delivery systems alone as well as in combination with a fibrous scaffold that more closely mimics the structure of the cartilage ECM during development.

NaCS Hydrogel and Fibrous-Gel Scaffold

In one embodiment, NaCS is used as the main hydrogel component for tissue scaffold constructs. One commercially available NaCS has a sulfur level based on atomic mass of about 18%. This suggests that on average, each glucose residue in the polysaccharide is substituted with slightly more than two sulfate groups as shown in FIG. 2. The water soluble cellulose compounds of the present invention comprise about 6 wt % to about 21 wt % of sulfur. Preferably, the compounds comprise about 12 wt % to about 18 wt % of sulfur.

Figure 3:
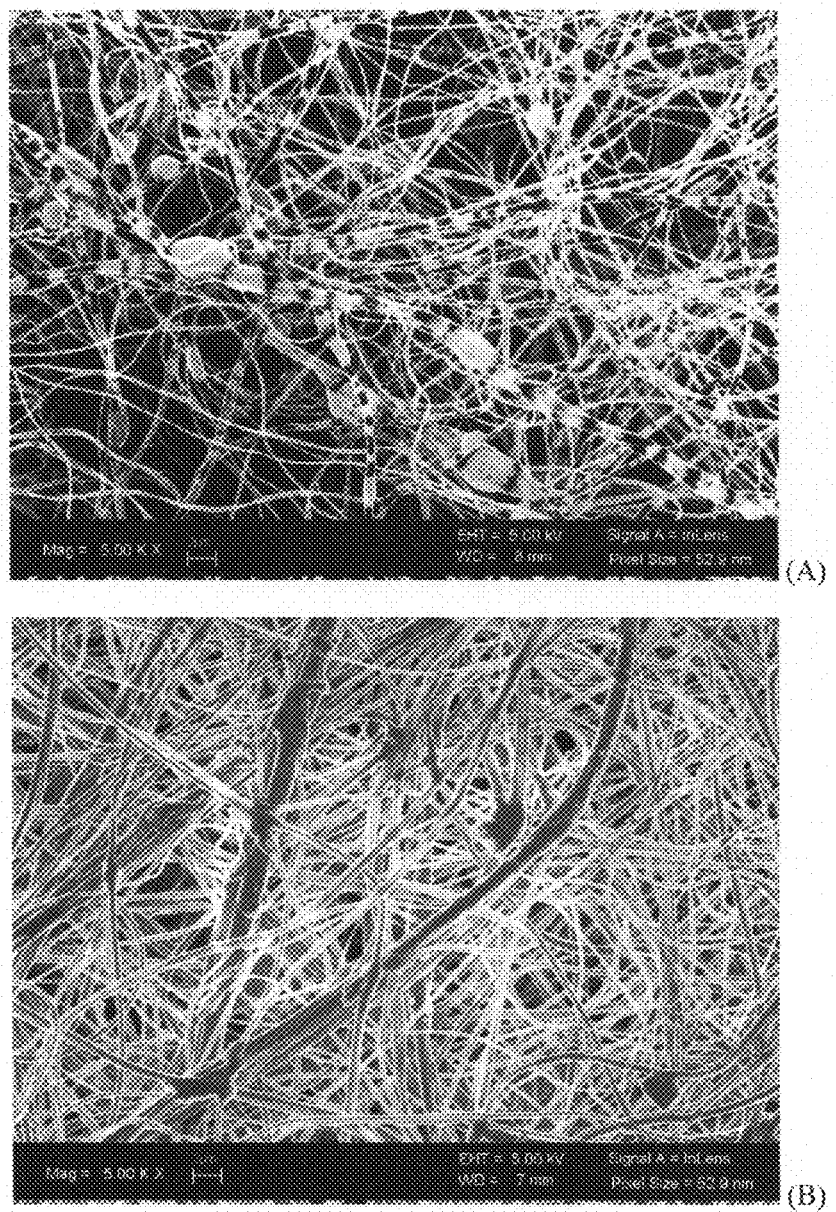
FIG. 3 shows SEM images of electrospun NaCS fibers, (A) immediately after spinning and (B) after air drying for 7 days.

At low concentration in aqueous media, NaCS forms a viscous solution. At higher concentrations, it forms a stiff gel. To demonstrate that NaCS could be electrospun into fibrous form, a 7% by weight solution of NaCS in water/dimethylformamide (DMF) (80/20 w/w) was prepared. FIG. 3(A) shows the scanning electron microscopy (SEM) images of the fibrous mat that results from electrospinning the solution at 30 kV using a 22 gauge needle with a needle to collecting plate distance of 20 cm. FIG. 3(B) shows the same electrospun sample after air drying for about 7 days. The change in visual texture that is observed is thought to be related to the fact that the material is electrospun as hydrogel filaments, and that after several days of air drying, the water evaporates leaving dry fibers. The "zebra-like" stripe patterns and the bulges that are apparent in the filaments before they dry are taken to be indicative of the presence of water in the hydrogel structure. The results of these experiments indicate that NaCS can be electrospun and therefore incorporated in multiple embodiments of the present invention.

Preferably, the water soluble cellulose compound solutions for electrospinning into fibers comprise from about 1 wt % to about 20 wt % of water soluble cellulose compound. More preferably, the solutions comprise from about 4 wt % to about 10 wt % of water soluble cellulose compound. With respect to NaCS, preferably the solutions comprise from about 2 wt % to about 15 wt % of NaCS. More preferably, the solutions comprise from about 5 wt % to about 8 wt % of NaCS.

Figure 4:
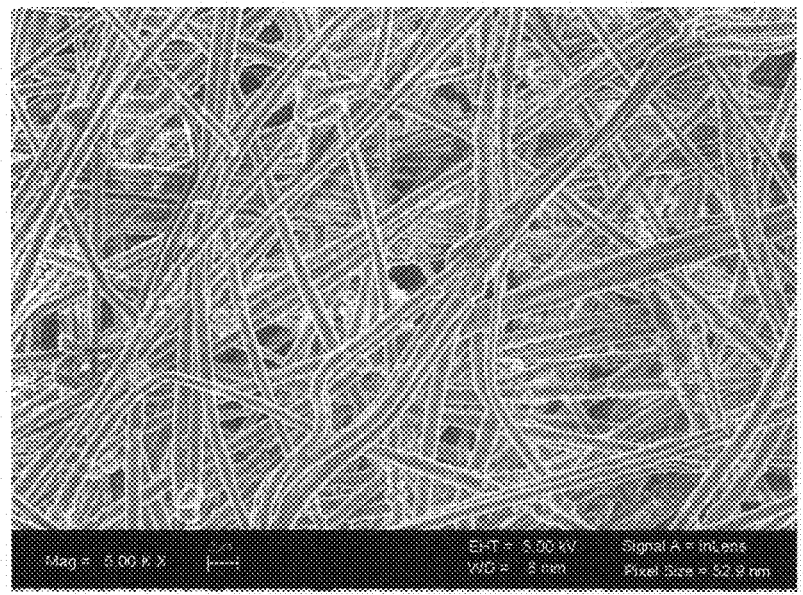
FIG. 4 shows SEM images of electrospun fibers from (A) 5% NaCS with 0.6% $CaCl_2$, and (B) 7% NaCS/bovine gelatin.
Figure 4:
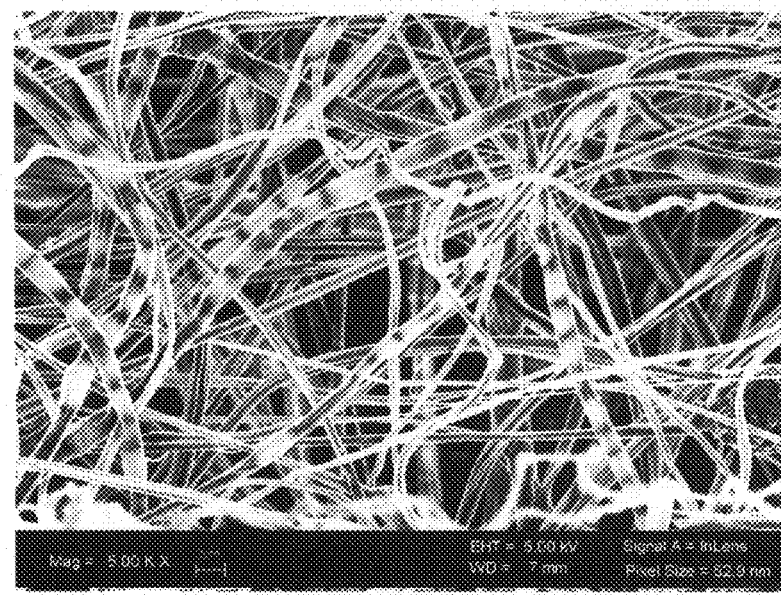

In one example, variations on this protocol were attempted to assess the possibility of electrospinning NaCS with other components that might be useful in scaffold fabrication. FIG. 4(A) shows the SEM image of fibers produced when approximately 5% NaCS solution in water/DMF (80/20) was electrospun with approximately 0.6% (w/w) $CaCl_2$. Calcium chloride was used as the ionic crosslinking agent. At this low level the calcium chloride was found not to be effective for the electrospun material. The angular particulates observed in the SEM were taken to be ionic crystals of $CaCl_2$ or NaCl, which could form if sodium ions are displaced by calcium. FIG. 4(B) shows the SEM image of fiber produced from a 7% NaCS/Bovine gelatin (3/1 w/w) in water/DMF (80/20). This experiment demonstrates the ability to electrospin a blend of the denatured collagen protein and the hydrogel material. This is a useful method to crosslink the collagen gel and the NaCS hydrogel. The insoluble, fibrous scaffold construct made in this facile manner contains both the amino acid sequences that facilitate cell attachment and the hydrogel component to deliver growth factors. The "zebra-like" texture apparent in FIG. 4(B) is consistent with previous observations that the NaCS/Bovine gelatin material is deposited as a hydrogel filament. In certain embodiments, the ratio of NaCS/Bovine gelatin is from about 1:10 to about 10:1 (w/w).

Figure 5:
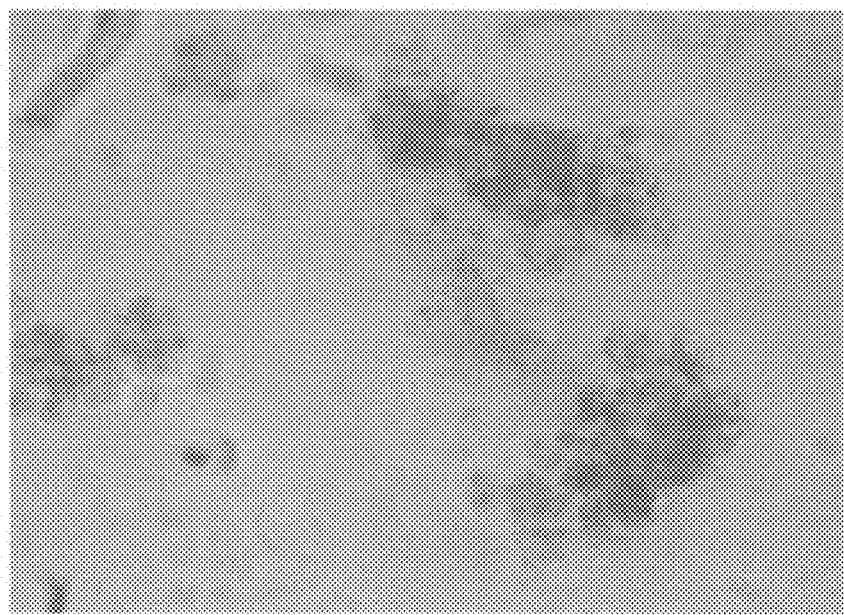
FIG. 5 shows light microscopy images of human MSCs in NaCS gel (not cross-linked) forming aggregates, 10× objective.

In another exemplary embodiment, a fibrous network-hydrogel tissue scaffold construct was fabricated by using a vacuum to draw an approximately 7% NaCS solution in water/DMF through a poly L-lactic acid (PLLA) electrospun mat. A PLLA mat treated in this manner has NaCS hydrogel material coating the filaments of the mat and occupying the interstices between the filaments. In a preferred embodiment, the NaCS/PLLA matrix is seeded with a stem/progenitor cell. In another exemplary embodiment, hMSCs were seeded onto a NaCS gel prepared with phosphate buffered saline (PBS, ph 7.4) placed directly into the well plate. The NaCS hydrogel was not cross-linked. The light microscope image in FIG. 5 indicates that on the NaCS hydrogel solution cells did aggregate. However, assays indicated a low number of cells on the hydrogel and on the PLLA-hydrogel construct after 7 days in culture (two media exchanges). Observations during the experiment suggested that because of the solubility of the NaCS in the incubation media, cells were likely washed away during media exchanges. In certain embodiment, the hydrogel to PLLA weight ratio ranges from about 0.5 to 30. In a preferred embodiment, the hydrogel to PLLA weight ration is about 1 to 5.

Figure 6:
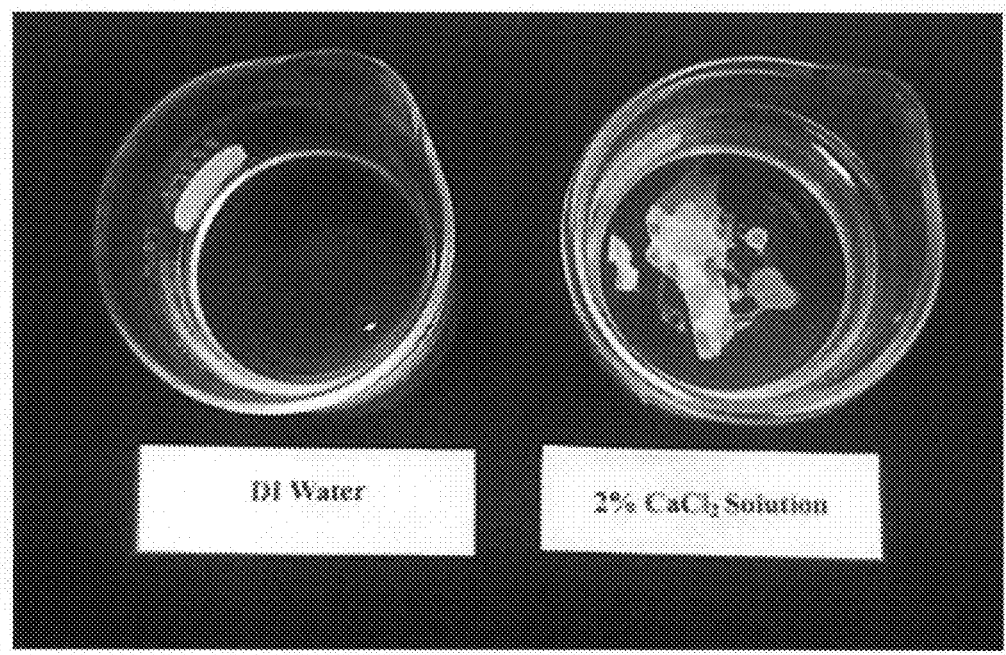
FIG. 6 shows images of 7% NaCS films immersed in DI water or DI water containing 2% $CaCl_2$. The white solid films in the $CaCl_2$ solution are insoluble, ionically crosslinked NaCS film. In DI water, the NaCS films dissolved.
Figure 7:
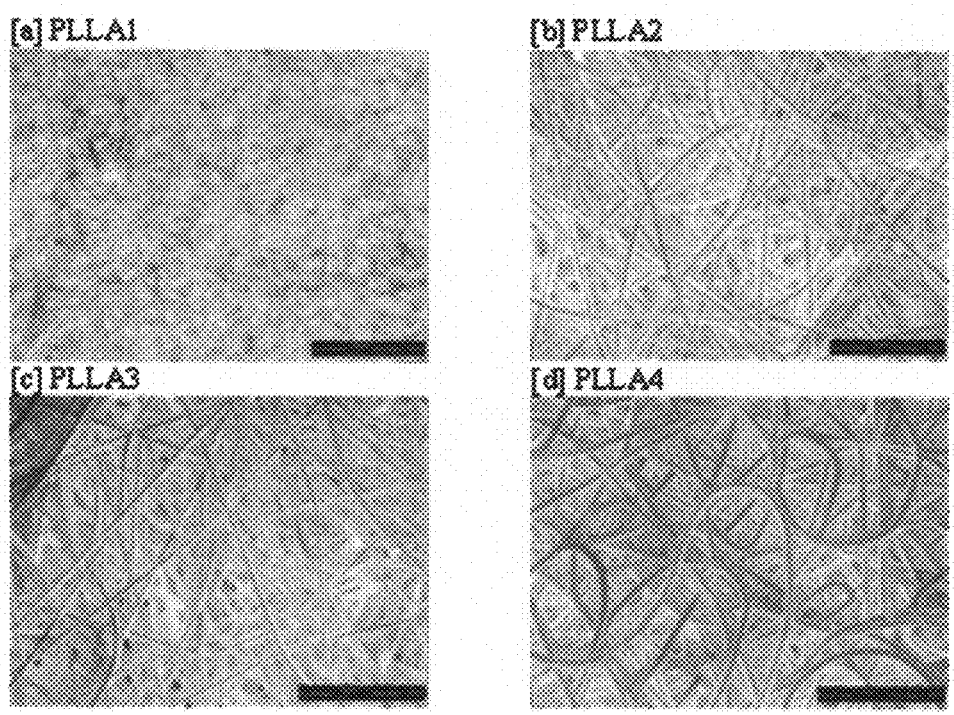
FIG. 7 shows SEM images of electrospun PLLA having well-controlled fiber diameters of (A) PLLA1, 290±84 nm, (B) PLLA2, 1±0.4 μm, (C) PLLA3, 5±1.5 μm, and (D) PLLA4, 9±2 μm. All images are 650× magnification.

To address the solubility in this example, NaCS was crosslinked to increase gel stability. Here, ionic crosslinking was performed using abivalent (i.e., divalent) cation available in a water soluble salt, for example bivalent calcium (e.g. $CaCl_2$). In FIG. 6, films of 7% NaCS in DI water, cast, air dried, and immersed in solutions of DI water or DI water containing 2% $CaCl_2$ are shown. The white solid in the $CaCl_2$ solution is the insoluble, ionically crosslinked NaCS film. Nothing is visible in the DI water, because in the absence of the $CaCl_2$, the NaCS film dissolved. Therefore, in an additional embodiment, the invention provides a scaffold comprising a soluble cellulose material, for example, NaCS, cross-linked by a bivalent cation, e.g., $Ca^{2+}$, $Ba^{2+}$, $Mg^{2+}$, $Fe^{2+}$, $Cu^{2+}$. In a preferred embodiment, the bivalent cation is calcium.

The range of $CaCl_2$ in DI water for these procedures is 0.5 to 5 wt %. Effective crosslinking was achieved using $CaCl_2$ concentrations of 2% or greater. Because each Ca2+ cation can complex with two sulfate groups on the sodium cellulose sulfate, the extent of complexation, which is related to the degree of crosslinking is expected to be high.

Fabrication and Characterization NaCS Hydrogels and Gel-Fiber Constructs.

Figure 13:
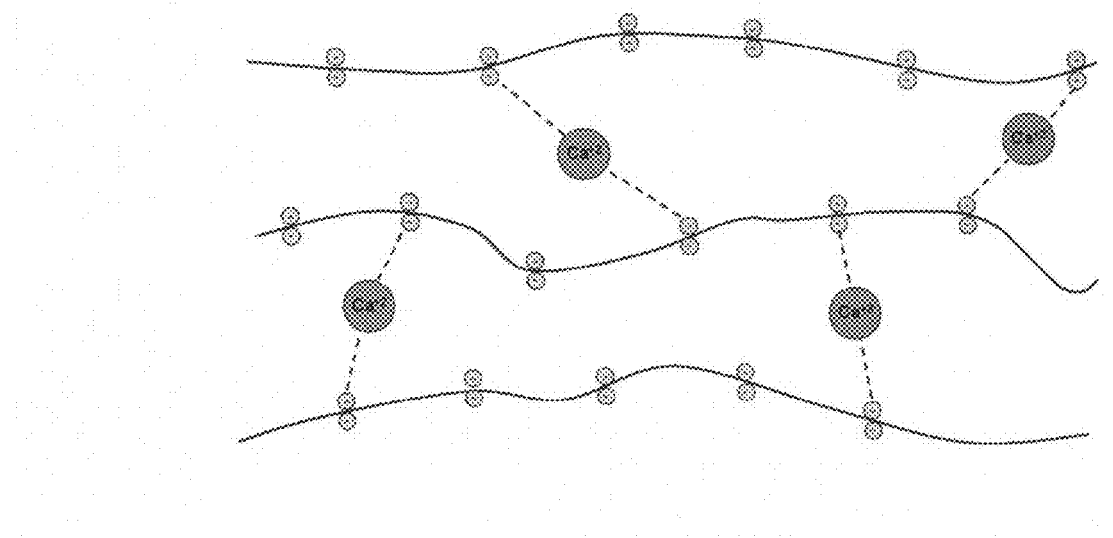
FIG. 13 shows a diagram of the mechanism for cross-linking NaCS.

The characterization of NaCS hydrogels and gel-fiber constructs have been performed. FIG. 13 shows a representation of the mechanism of crosslinking NaCS with bivalent calcium. It is important to note that crosslinking can be achieved without complexing all the available sulfate groups. A crosslinking process involving all available sulfates groups would be so extensive that the material would become brittle and be unable to absorb water. There are indications that the Ca-crosslinked NaCS remains a flexible hydrogel suggesting that functional sulfates groups remain available. Other ionic cross-linking agents could be used such as $MgCl_2$. In certain embodiment, the hydrogel comprises soluble cellulose, e.g., NaCS, fiber matrix in which one or more fibers are cross-linked by a bivalent cation.

In another embodiment of the present invention, NaCS gels will be cast from PBS solutions (in order maintain a pH of 7.4) prepared at from approximately 5% to approximately 10% concentrations (w/w). Films/disks may be air or vacuumed dried and crosslinked by immersing them into $CaCl_2$ solutions. In certain embodiments, the NaCS hydrogel films will be crosslinked using $CaCl_2$ solutions that range in concentration from approximately 0.5% (w/w) to saturation.

In certain aspects, the scaffold comprises PLLA fibers. In an exemplary embodiment, PLLA will be electrospun according to protocols (See Shanmugasundaram S, Arinzeh T L. Regulation of human mesenchymal stem cell chondrogenesis by scaffold geometry and mechanical properties. Society for Biomaterials Annual Meeting, 2009). In certain embodiments, the fibers formed have an average diameter of from about 500 nm to about 10 μm. In a further embodiment, the fibers formed are micron-sized fiber diameters, of from about 2 μm to about 7 μm. In another embodiment, the fibers formed have an average diameter of about 5 μm. Micron sized fibers are generally preferred, however, to facilitate cell infiltration and tissue ingrowth. NaCS gels will be cast onto fibrous mesh, subjected to vacuum, and cross-linked using a $CaCl_2$ solution. Static and dynamic compression tests will be performed of the fiber-gel construct versus fibrous scaffold alone, according to previously published protocols (See Bian L. Kaplun M, Williams D Y, Xu D, Ateshian G A, Hung C T. In any embodiment described herein, the hydrogel/fiber structure may optionally include chondroitin sulfate.

Seeding or loading of cells for in vitro and in vivo use, may be performed by any technique known to one skilled in the art. Three exemplary approaches are described herein. In one exemplary embodiment, NaCS powder is mixed with human MSCs in PBS and cross-linked using the optimized concentration of $CaCl_2$. In another exemplary embodiment, an NaCS gel is prepared and is vacuum loaded, using a previously reported technique (See Livingston T L, 2003; 85-A(10): 1927-35), with MSCs in PBS and then cross-linked using the optimized concentration of $CaCl_2$. In another exemplary embodiment, cross-linked NaCS gel will be vacuum loaded with MSCs. In one embodiment, the cell seeding density is about $2.5 \times 10^6$ cells/mL, which is based upon studies evaluating chondrogenesis in pellet cultures. (See Mackay A M, Beck S C, Murphy J M, Barry F P, Chichester C O, Pittenger M F. Chrondrogenic differentiation of cultured human mesenchymal stem cells from marrow. Tissue Engineering 1998; 4(4):415-28). Metabolic activity and cell growth over time will be measured using the XTT kit according to the manufacturer's instructions (Biotium, USA).

In other embodiments, the biological function of NaCS in immobilizing growth factors similar to other sulfated glycosaminoglycans is utilized. (See Ishihara M, Sato M, Hattori H, Saito Y, Yura H, Ono K, et al. Heparin-carrying polystyrene (HCPS)-bound collagen substratum to immobilize heparin-binding growth factors and to enhance cellular growth. J Biomed Mat Res 2001; 56(4):536-44). Growth factors are naturally occurring substances capable of stimulating cellular growth, proliferation, repair and cellular differentiation. Usually, the growth factor is a protein or small molecule, e.g., a steroid hormone, that bind to specific receptors on the surface of their target cells. Growth factors are important for regulating a variety of cellular processes and typically act as signaling molecules between cells. Growth factors include, for example, bone morphogenic proteins, while fibroblast growth factors and vascular endothelial growth factors stimulate blood vessel differentiation (angiogenesis).

A non-exclusive list of exemplary growth factors that can be used in any of the embodiments described herein include: Autocrine motility factor, Bone morphogenetic proteins (BMPs), Epidermal growth factor (EGF), Erythropoietin (EPO), Fibroblast growth factor (FGF), Granulocyte-colony stimulating factor (G-CSF), Granulocyte-macrophage colony stimulating factor (GM-CSF), Growth differentiation factor-9 (GDF9), Hepatocyte growth factor (HGF), Hepatoma derived growth factor (HDGF) Insulin-like growth factor (IGF), migration-stimulating factor, Myostatin (GDF-8), Nerve growth factor (NGF), brain-derived neurotrophic factor (BDNF) and other neurotrophins, Platelet-derived growth factor (PDGF), Thrombopoietin (TPO), Transforming growth factor alpha (TGF-α), Transforming growth factor beta (TGF-β), Vascular endothelial growth factor (VEGF), placental growth factor (PlGF), and/or Foetal Bovine Somatotrophin (FBS).

In one embodiment, TGF-β3 may be included in the scaffold matrix. It is routinely used in chondrogenic induction media for human MSCs and is detected during chondrogenesis during development in vivo. Immobilization is detected based on previously reported protocols. (See Ishihara M.). Immobilization studies used for different embodiments are as follows: various concentrations of TGF-β3 in BSA-PBS are added to cross-linked NaCS films overnight at 4° C. Wells are washed with BSA-PBS and immunofluorescent staining is performed using mouse anti-human TGF-β3 (Abcam, Inc.) followed by secondary, anti-mouse IgG conjugated with FITC (BD Biosciences, Inc). Fluorescent intensity is then detected using a fluorescent plate reader (FLX800, Biotek, Inc.) and correlated with the amount.

In certain circumstances, NaCS using ionic-crosslinking may not form a stable gel long-term. In another embodiment, the functional structure of the NaCS can be preserved and unaltered by entrapping it in a hydrogel network formed by a non-functional soluble polysaccharide. Therefore, in another embodiment, a soluble cellulose material, e.g., NaCS, may be co-dissolve with a non-functional soluble polysaccharide, e.g., dextran, forming a mixture that can be selectively crosslinked by chemical means. Since NaCS is highly substituted, there are few sites available for crosslinking. Dextran, however, is a fully unsubstituted polysaccharide and can undergo facile crosslinking using chemical agents such as sodium trimetaphosphate (STMP) or diglycidyl ether compounds. (See Lack S, Dulong V, Picton L, Cerf D L, Condamine E. High-resolution nuclear magnetic resonance spectroscopy studies of polysaccharides crosslinked by sodium trimetaphosphate: a proposal for the reaction mechanism. Carbohydrate Research 2007; 342(7):943-53; See also Collins M N, Birkinshaw C. Comparison of the effectiveness of four different crosslinking agents with hyaluronic acid hydrogel films for tissue-culture applications. Journal of Applied Polymer Science 2007; 104(5):3183-91; See also Rogovina S Z, Akopova T A, Vikhoreva G A, Gorbacheva I N. Solid state production of cellulose-chitosan blends and their modification and the diglycidyl ether of oligo(ethylene oxide). Polymer Degradation and Stability 2001; 73(3):557-60). The result is a fully functional NaCS entrapped in a crosslinked dextran hydrogel. Other embodiments of the present invention may be directed to the use of the polyanion properties of NaCS to complex it with a polycation. For example, a hydrogel matrix can be formed by complexing NaCS with chitosan. This approach has been demonstrated in the fabrication of nanoparticles from chitosan and dextran sulfate. (See Chen Y, Siddalingappa B, Chan P H, Benson H A. Development of a chitosan-based nanoparticle formulation for deliver of a hydrophilic hexapeptide, dalargin. Biopolymers 2008; 90(5): 663-70).

Electrospinning

Electrospinning process produces meshes with high surface area, controllable porosity, architecture and mechanical properties. Any electrospinning process known to one skilled in the art may be used. For example, the electrospinning setup used in the present invention comprises a syringe fitted with a needle (16-22 gauge), mounted on a Harvard Syringe Pump Model 901. The syringe is filled with the polymer solution and a constant flow rate is maintained using the syringe pump. The positive output lead of a high voltage power supply (Gamma High Voltage Power Supply ES30P) is attached to the needle. The collector used is a stainless steel plate, which is electrically grounded. The electrospinning process is affected by varying the electric potential, flow rate, solution concentration, capillary-collector distance, diameter of the needle, and ambient parameters like temperature and humidity. When the charge of the polymer at increasing voltage exceeds the surface tension at the tip of the needle, the polymer is splayed randomly as fibers. The fibers are collected as non-woven mats at the collector.

Fiber diameter has an affect on human MSC chondrogenic differentiation. To date, research has focused only on meshes at the nanoscale (See Li W J, Tuli R, Huang X, Laquerriere P, Tuan R S. Multilineage differentiation of human mesenchymal stem cells in a three-dimensional nanofibrous scaffold. Biomaterials 2005; 26(5):5158-66; See also Xin X, Hussain M, Mao J J. Continuing differentiation of human mesenchymal stem cells and induced chondrogenic and osteogenic lineages in electrospun PLGA nanofiber scaffold. Biomaterials 2007; 28(2):316-25) or at the micron scale (See Li W J, Cooper J A, Mauck R L, Tuan R S. Fabrication and characterization of six electrospun poly(alpha-hydroxyester)-based fibrous scaffolds for tissue engineering applications. Acta Biomaterialia 2006; 2(4):377-85) for cartilage applications. In any of the embodiments described herein, electrospun scaffolds of poly L-lactic acid (PLLA) may be fabricated with well-controlled fiber diameters on the order of 100 nm up to 10000 nm (FIGS. 7(A)-(D)) (See Shanmugasundaram). Their average fiber diameters and corresponding mean pore sizes, as determined by capillary flow porometry (PMI, Inc.) are listed in Table 1.

Figure 8:
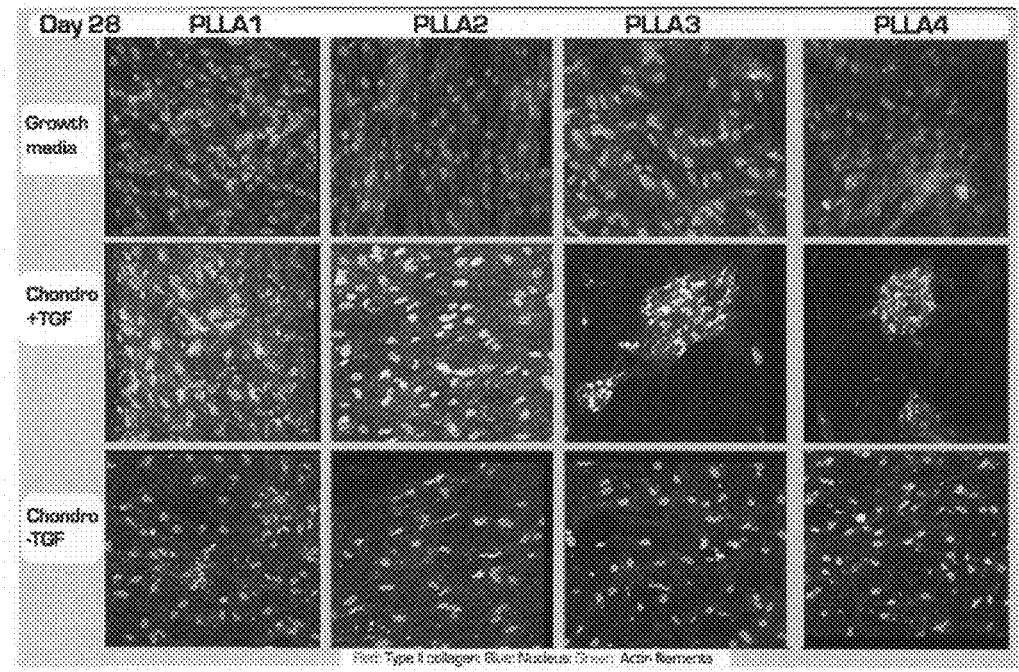
FIG. 8 shows confocal microscopy images of human MSCs cultured on PLLA 1-4 scaffolds in standard growth media (top row), CCM+=chondrogenic culture media with TGF-β3 (middle row), or CCM-=chondrogenic culture media without TGF-β3. Type II collagen is stained in red. Nucleus is blue and actin filaments are green. All images take with a 20× objective.
Figure 10:
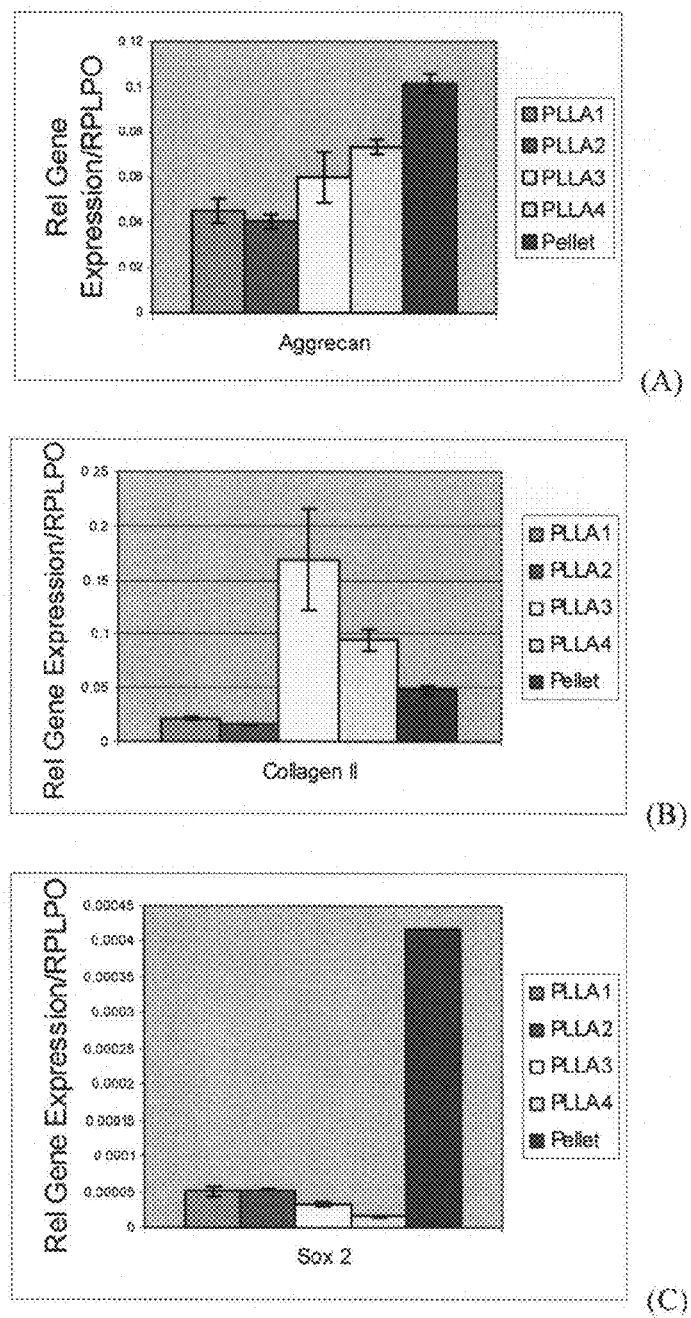
FIG. 10 shows gene expression of human MSCs cultured for 28 days on PLLA having varying fiber diameters, PLLA1-PLLA4. Cell pellet cultures served as positive control. All were cultured in CCM+=chondrogenic culture media with TGF-β3. (A) Aggrecan, (B) Collagen type II and (C) Sox 2

The porosities for all scaffolds were approximately 80% to 90%. As shown in confocal microscopy images in FIG. 8, human MSCs seeded at high densities on scaffolds formed aggregates on micron-sized fibers in the presence of CCM+ media (chondrogenic culture media with TGF-β3) on day 28. Also, noteworthy, the aggregates could be detected in other planes within the scaffold. Cells on nanofiber sized scaffolds remained well-spread in a single layer on the top surface. Late stage chondrogenic markers of Collagen Type II and aggrecan were expressed at the highest levels on micron-sized fiber diameters (PLLA-3 and PLLA-4) (FIGS. 10(A) and (B)). GAG synthesis was also highest for micron-sized fibers, $p<0.05$. Interestingly, the gene expression of Sox2 was also examined, which is a marker expressed in undifferentiated human MSCs (See Greco S, Zhou C, Ye J H, Rameshwar P. An interdisciplinary approach and characterization of neuronal cells transdifferentiated from human mesenchymal stem cells. Stem cells and development 2007; 16(5):811-26)(FIG. 10.c.). Sox2 was expressed at low levels on all fibrous scaffolds as compared to pellet cultures and PLLA films, indicating that the fibrous structure may also direct, in part, stem cell differentiation as opposed to self-renewal.

TABLE 1

Average fiber and pore diameters of PLLA1-4.

| Polymer | Average Diameter | Average Pore Size |
|---------|------------------|-------------------|
| PLLA-1 | 290 ± 84 nm | 2.4 ± 1.1 μm |
| PLLA-2 | 1 ± 0.4 μm | 3.3 ± 1.8 μm |
| PLLA-3 | 5 ± 1.5 μm | 27.2 + 22.4 μm |
| PLLA-4 | 9 ± 2.0 μm | 29.1 ± 17.7 μm |

Figure 9:
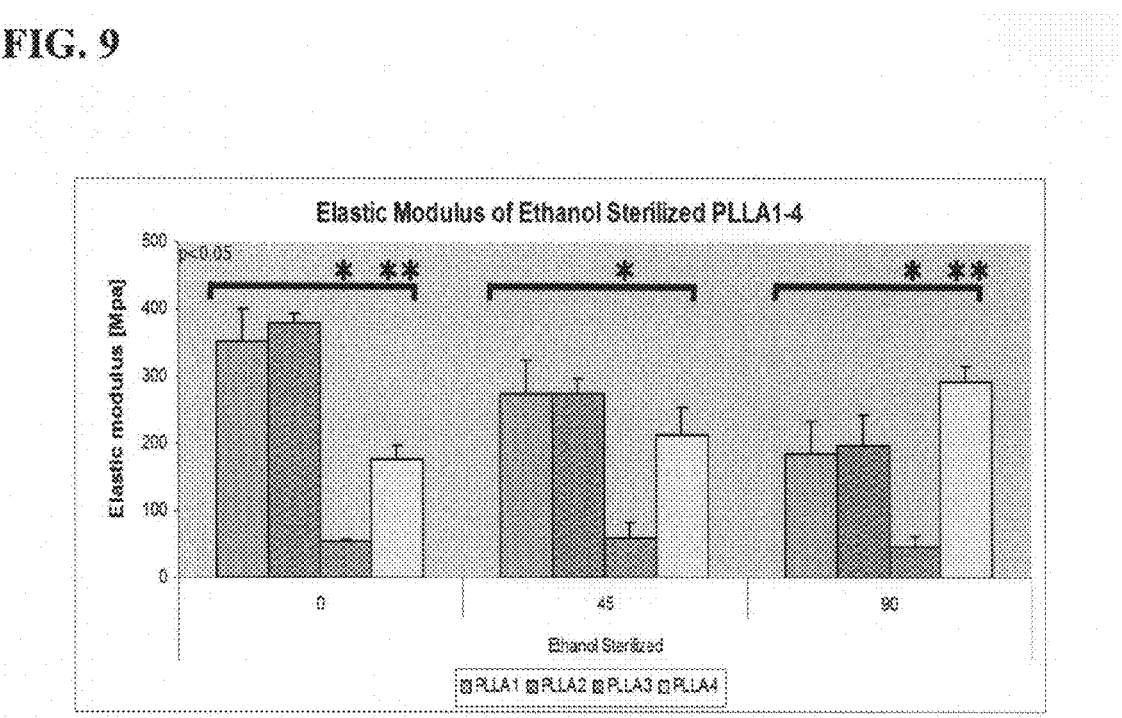
FIG. 9 shows the elastic modulus of sterilized PLLA 1-4 electrospun mats tested in tension under wet conditions. Mats were cut at 00, 45° and 90° angles and immersed in PBS. *$p<0.05$, PLLA-3 is significantly lower than all other materials. **$p<0.05$, PLLA-4 is significantly different from all other materials.

To assess the mechanical properties of the PLLA mats, the mats were cut at 0°, 45° and 90° angles and immersed in phosphate buffered saline (PBS) at 37° C., 5% $CO_2$ for a day prior to testing with Instron Tensile tester. The elastic modulus for PLLA-3 (5 μm fiber diameter) (FIG. 9) was significantly lower than all other scaffolds and corresponded to the tensile modulus of normal, human articular cartilage of the femoral condyles. (See Temple M M, Bae W C, Chen M Q, Lotz M, Amiel D, Coutts R D, et al. Age- and site-associate biomechanical weakening of human articular cartilage of the femoral condyle. Osteoarthritis and Cartilage 2007; 15:1042-52).

The following examples are put forth so as to provide those of ordinary skill in the art with a complete disclosure and description of how to make and use the present invention, and are neither intended to limit the scope of what the inventors regard as their invention nor they intended to represent that the experiments below are all or the only experiments performed

EXAMPLES

Materials and methods useful for practicing the present invention may be further described in one or more of the following: U.S. Pat. Nos. 6,689,166; and 6,790,528; and U.S. Published Pat. App. Nos. 2004-0018226; 2006-0204539; 2009-0325296; 2009-0028921; and 2006-0128012, the disclosures of which are all incorporated herein by reference in their entirety for all purposes.

Investigation of the Chondrogenic Differentiation of Human MSCs on Na—CS In Vitro.

NaCS is structurally similar to glycosaminoglycans such as the chondroitin sulfates, dermatan sulfate, keratin sulfate and heparin. Based on these structural similarities, NaCS will impart functional qualities that are similar to the functions of the glycosaminoglycans. NaCS either used alone or with a fibrous network support and/or direct human MSC chondrogenesis. Embodiments of the present invention demonstrate that human MSCs on fibrous meshes grow and express enhanced levels of mature chondrocytic markers and a reduction in Sox2 expression, which is characteristic for an undifferentiated MSC.

Figure 11:
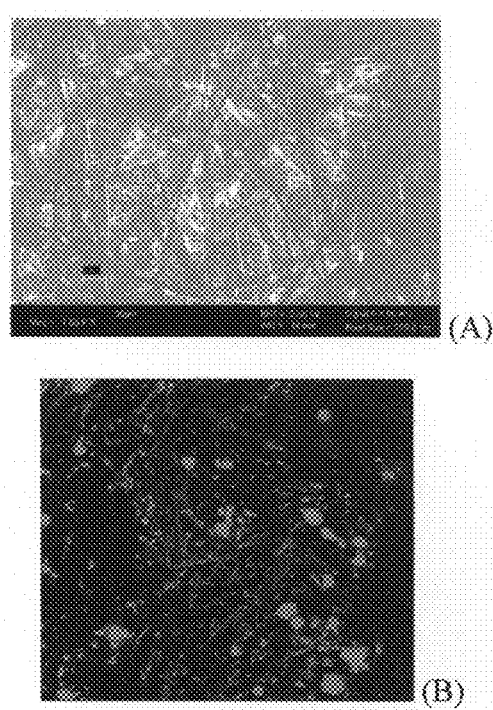
FIG. 11 shows an (A) SEM micrograph image of electrospun, thick scaffolds for in vivo use and a (B) confocal image of cross-section of rab MSCs loaded onto scaffolds. Cells are stained with DiI, a cytoplasm stain—cells appear large and rounded in morphology. Images take with a 40× objective.

Traditional electrospinning has the limitation of producing sheet-like scaffolds or membranes due to the nature of the process, which, in turn, may limit its use in vivo. In maximizing the effectiveness of electrospinning, an improved electrospinning technique for the fabrication of thick, continuous electrospun scaffolds may be used (i.e. greater than 3 mm in thickness) (FIG. 11(A)).

Figure 12:
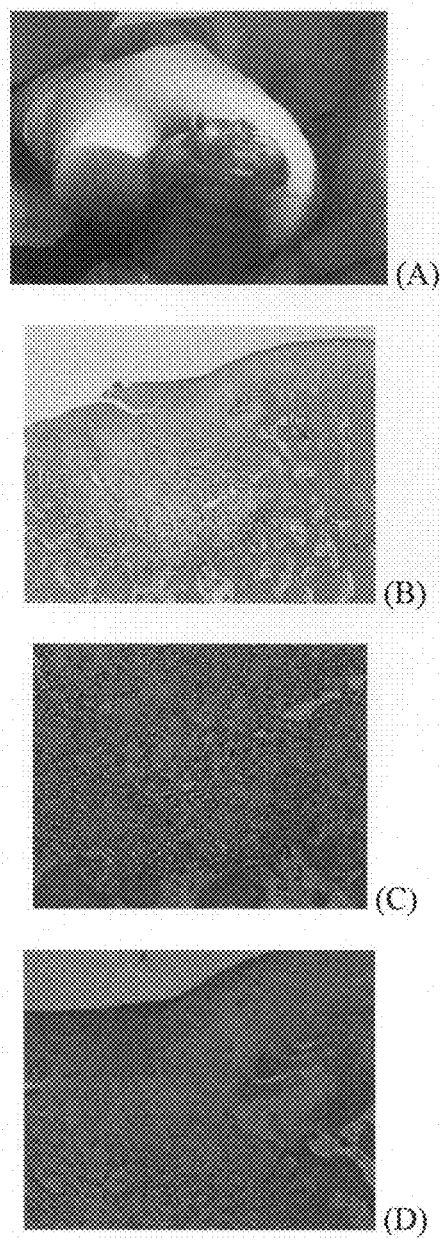
FIG. 12 shows (A) an image of an osteochondral defect in the medial femoral condyle of the rabbit. Histological images of electrospun PLLA scaffolds at 12 weeks post-op; (B) a cross-section, H&E stain, 4× objective; (C) 10× objective, yellow rectangle, and (D) 10× objective, green rectangle. The arrow points to a histological artifact.

The technique uses a two power supply setup, in contrast to the commonly used one power supply setup. This novel setup creates a stronger and more focus electrostatic field, which becomes the driving force for the process. Rabbit mesenchymal stem cells (rabMSCs) were then loaded onto the scaffolds and were determined to be evenly distributed throughout the thickness of the scaffold using confocal microscopy (FIG. 11(B)). The scaffold was inserted by press-fit technique into a 3 mm diameter osteochondral defect in the medial femoral condyle in the rabbit (FIG. 12(A)). Histological evaluation of PLLA electrospun scaffolds at 12 weeks post-implantation demonstrated cartilage formed within the scaffold (FIG. 12(B)-(D)). Cells were round, embedded in lacunae and having a clustering appearance similar to the native cartilage. Scaffold was contiguous with host tissue. The outer surface of the defect was continuous with the host, but it had the appearance of a mixture of fibrous and cartilage tissue.

Human MSC chondrogenesis may be optimized using hydrogels alone, PLLA-hydrogel constructs, or PLLA scaffolds. In any of the embodiments described herein, hydrogels may be immobilized/preconditioned with TGF-β3 prior to cell seeding.

Differentiation of MSCs in micromass pellet cultures (positive control) or seeded onto scaffolds is assessed using biochemical, histochemical and molecular biology techniques. Comparisons are made with articular chondrocytes. For example, transcriptional factors and markers of early and late stage chondrocytes, hypertrophic chondrocytes and osteoblasts may be compared as an indicator of differentiation.

Bone marrow is processed according to previously published protocols. (See Bruder S P, Kurth A A, Shea M, Hayes W C, Jaiswal N, Kadiyala S. Bone Regeneration by Implantation of Purified, Culture-Expanded Human Mesenchymal Stem Cells. J Orthop Res 1998; 16:155-62). Briefly, marrow samples are fractionated by centrifugation over a density cushion and plated on tissue culture flasks in Dulbecco's Modified Eagle's Medium (DMEM) containing 10% fetal bovine serum and 1% antibiotic (standard growth media). Cultures will be maintained at 37° C., 5% $CO_2$. Colony formation is monitored for a 14-17 day period and then, cells are subcultured. Cells are examined for morphology and cell surface markers typical for undifferentiated MSCs. (See Pitenger). Cells expressing CD44 and the absence of CD45 and CD34 surface antigens are verified by fluorescence-activated-cell-sorter. Human, articular chondrocytes are obtained from Asterand, Inc. and cultured using known protocols.

In certain embodiments, MSCs are seeded onto scaffolds, or grown in standard pellet cultures (as a positive control). Scaffolds tested will be hydrogels, PLLA-gel construct, PLLA alone, and TGF-β3 immobilized hydrogels and PLLA-gel constructs. They are cultured in serum-free chondrogenic complete medium (CCM+) consisting of 1 mM sodium pyruvate (Sigma), 0.1 mM ascorbic acid-2-phosphate (Wako), $1 \times 10^{-7}$ M dexamethasone (Sigma), 1% ITS+ (Collaborative Biomedical Products), and 10 ng/mL recombinant human TGF-β3 (Oncogene Sciences) dissolved in DMEM-low glucose for chondrogenesis, CCM without TGF-β3 (CCM−) or standard growth media. Comparisons are made with articular chondrocytes grown in the same pellet culture conditions using CCM+ media, as a positive control.

In certain exemplary embodiments, proliferation is evaluated at Days 7, 14, and 28 days in all scaffold groups and controls. Proliferation and metabolic activity is evaluated by DNA quantitation and MTT assay (as described in the preliminary results section). For chondrogenesis, chondrogenic pellets formed from MSCs and chondrocytes and cell-laden scaffolds will be harvested at 7, 14, and 28 days and analyzed for glycosaminoglycan, Type II collagen, and proteoglycan synthesis. Glycosaminoglycan and proteoglycan synthesis is measured quantitatively using an ELISA kit (Blyscan™ Kit, Accurate Chemical and Scientific Corporation, Westbury, N.Y.). Highest levels in control pellets can be expected by day 14. (See Barry F, Boynton R E, Liu B, Murphy J M. Chondrogenic differentiation of mesenchymal stem cells from bone marrow: differentiation-dependent gene expression of matrix components. Experimental Cell Research 2001; 268: 189-200). Type II collagen synthesis may be measured by an ELISA kit (Arthrogen-CIA, Chondrex, Inc.).

Histological staining and confocal microscopy is performed of the pellets and cell-laden scaffolds at days 7, 14 and 28. For histology, the pellets are fixed in formalin 10%, dehydrated through graded alcohols, and embedded in paraffin. For example, sections are cut at a thickness of about 5 µm and stained with Alcian blue, Safranin-O, and Sirius Red. Alcian Blue stains both sulfated and carboxylated acid mucopolysaccharides and sulfated and carboxylated sialomucins. Safranin O in the orthochromatic form stains articular cartilage, mucin and mast cell granules on formalin-fixed, paraffin embedded tissue sections. Proteoglycans will stain red, cytoplasm will stain gray green and nuclei will stain black. Sirius Red dye can be used to differentiate different collagen types in tissue sections. Confocal microscopy may be utilized to visualize the cell interaction and overall morphology of the cells on the scaffolds using actin cytoskeleton stain (Alexa Fluor 488 phalloidin; Invitrogen, USA) and a nuclear stain ((4',6-diamidino-2-phenylindole, DAPI; Invitrogen, USA).

Real-time RT-PCR may also be performed to assay for the gene expression of early markers of fibromodulin and cartilage oligomeric matrix protein, mid-stage markers of aggrecan and versican, mature chondrocyte markers for type II collagen and chondroadherin, and sox9, a transcription factor, at, e.g., days 1, 14 and 28 days. Additional factors that may be analyzed are Sox-2, Oct-4 and NANOG as a marker for the undifferentiated MSC, as an indicator of stem cell self-renewal and maintenance. (See Greco S J, Liu K, Rameshwar P. Functional similarities among genes regulated by oct-4 in human mesenchymal and embryonic stem cells. Stem Cells 2007; 25(12):3143-54). Chondrocyte hypertrophic markers of Type X collagen, Type I collagen, matrix metalloproteinase 13, vascular endothelial growth factor (VEGF) and alkaline phosphatase will also be examined. (See Mueller). Gene expression at day 0 for MSCs and chondrocytes is also examined. Quantitative RT-PCR analysis may be performed with the One Step QuantiTect SYBR Green RT-PCR Kit (Qiagen, CA, USA) using the MX4000 detection system (Stratagene, CA, USA), according to the manufacturers' instructions.

Briefly, cells on scaffolds are harvested. Total RNA is isolated using the RNeasy Mini Kit (Qiagen) including the homogenization (QIA Shredder; Qiagen) and DNA digestion step (RNase Free DNase Set; Qiagen). The reverse transcription step will run for 30 min at 50° C., followed by PCR activation for 15 min at 95° C. Forty amplification cycles are run, consisting of 15 s denaturation at 94° C., 30 s of annealing at 55° C., and 30 s of extension at 72° C. For each reaction, a melting curve analysis of the RT-PCR product can be included. Samples are assayed in triplicate and the values are normalized to the relative amounts of the housekeeping gene RPLPO (ribosomal protein, large, PO) according to Muller et al. (See Muller P Y, Janovjak H, Miserez A R, Dobbie Z. Processing of gene expression data generated by quantitative real-time RT-PCR. Biotechniques 2002; 32(6):1372-4).

Protein level expression for Oct-4, Sox-2, and Nanog can be evaluated, e.g., using western analysis. (See Greco). Briefly, rabbit anti-Oct4, -SOX-2, -NANOG, and fluorescein isothiocyanate (FITC)-goat anti-rabbit are purchased from Abcam (Cambridge, Mass.). Nuclear proteins can be extracted with the Nxtract kit according to the manufacturer's specified guidelines (Sigma-Aldrich). Total protein is determined with a Bio-Rad (Hercules, Calif.) DC protein assay kit. Extracts (15 µg) are treated with protease inhibitor and analyzed using 4%-20% SDS-polyacrylamide gel electrophoresis precast gels (Bio-Rad). Proteins are transferred onto membranes (PerkinElmer Life and Analytical Sciences) and incubated overnight with primary antibodies. Detection is performed with HRP-conjugated IgG. Primary and secondary antibodies are used at dilutions of 1/1,000 and 1/2,000, respectively. Membranes$^{are}$ stripped with Restore Stripping Buffer (Pierce, Rockford, Ill.) for reprobing with other antibodies. Cytoplasmic contamination of nuclear extracts is determined by reprobing the membranes with anti-ribosomal protein L28.

The experimental groups include MSCs seeded onto scaffolds and pellet cultures using MSCs and chondrocytes. All of these groups, except for the chondrocyte pellet culture, are cultured in either standard growth media (control), CCM+ or CCM−. Chondrocytes are cultured in CCM+ only. Unless otherwise stated, the quantitative assays will be performed on days 7, 14, and 28 or days 1, 14 and 28 days for gene expression. A sample size, n of 4, is generally used for all quantitative biochemical assays (glycosaminoglycan, Type II collagen, and proteoglycan) and histological analyses. A sample size, n of 9, is generally used for gene expression, since the studies are usually performed in a 96-well plate format. One way and two way ANOVAs are performed to test for statistical differences between groups at each time point and over time, respectively for p<0.05. The Tukey-Kramer Method, p<0.05, is used to perform multiple comparisons between groups.

Applications and alternative embodiments include, but are not limited to, an injectable gel for filling cartilage defects, for cartilage repair, joint repair, arthritis relief. The compostions of the present invention may also be combined with a fibrous scaffold for treating large defects. As described herein, the embodiments of the present invention useful to support and promote tissue and cartilage repair with or without the use of stem cells.

Unless defined otherwise, all technical and scientific terms used herein have the same meaning as commonly understood by one of ordinary skill in the art to which this invention belongs. Although any methods and materials similar or equivalent to those described herein also may be used in the practice or testing of the present invention, the preferred methods and materials are now described. All publications mentioned herein are incorporated herein by reference to disclose and describe the methods and/or materials in connection with which the publications are cited.

The embodiments and examples provided herein are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

We claim:

1. A fibrous network-hydrogel composition for use in tissue engineering comprising a matrix including a fibrous polymer network formed of at least one of an electrospun degradable polymer, an electrospun nondegradable polymer or a combination thereof, wherein the degradable polymer is poly L-lactic acid (PLLA), wherein the electrospun fibers have an average diameter between about 2 µm and about 7 µm and are coated with sodium cellulose sulfate (NaCS) wherein the sodium cellulose sulfate is ionically crosslinked onto the fibers, forms a hydrogel, and occupies at least a portion of the interstices between the fibers.

2. The fibrous network-hydrogel composition of claim 1, wherein the fibrous polymer network comprises a nondegradable polymer and a degradable polymer.

3. The fibrous network-hydrogel composition of claim 1, wherein the nondegradable polymer is selected from the group consisting of a polyurethane, a polyvinylidine fluoride, and a polyvinylidine fluoride trifluoroethylene.

4. The fibrous network-hydrogel composition of claim 1, further comprising stem cells.

5. The fibrous network-hydrogel composition of claim 4, wherein the stem cells are mesenchymal stem cells.

6. The fibrous network-hydrogel composition of claim 5, wherein the hydrogel promotes stem cell chrondrogenesis.

7. The fibrous network-hydrogel composition of claim 1, further comprising collagen.

8. The fibrous network-hydrogel composition of claim 1, further comprising a cell growth factor.

9. The fibrous network-hydrogel composition of claim 1, further comprising an unsubstituted soluble polysaccharide.

10. The fibrous network-hydrogel composition of claim 9, wherein the polysaccharide is dextran.

11. The fibrous network-hydrogel composition of claim 1, wherein the fibers have an average diameter of about 5 micrometers.

12. A fibrous network-hydrogel composition formed according to the method comprising: electrospinning at high voltage a fibrous network formed of at least one of degradable polymer, wherein the degradable polymer is poly L-lactic acid (PLLA), a nondegradable polymer or a combination thereof, wherein the fibers have an average diameter between about 2 µm and about 7 µm and coating the electrospun fibrous network with sodium cellulose sulfate (NaCS), wherein the sodium cellulose sulfate is ionically crosslinked onto the fibers, forms a hydrogel, and occupies at least a portion of the interstices between the fibers.

13. The fibrous network-hydrogel composition of claim 12, wherein the fibers have an average diameter of about 5 micrometers.

14. A method of treating or repairing cartilage tissue in a subject in need of such repair, the method comprising administering to said subject an effective amount of a hydrogel according to claim 1.

15. A method of treating arthritis in a subject in need of such treatment, the method comprising administering to said subject an effective amount of a hydrogel according to claim 1.

* * * * *